US008236949B2

(12) United States Patent
Fox et al.

(10) Patent No.: US 8,236,949 B2
(45) Date of Patent: Aug. 7, 2012

(54) TETRAZINE-BASED BIO-ORTHOGONAL COUPLING REAGENTS AND METHODS

(75) Inventors: Joseph Michael Fox, Wilmington, DE (US); Melissa Blackman, Elkton, MD (US); Maksim Royzen, Philadelphia, PA (US); Ni Yan, Glen Mills, PA (US)

(73) Assignee: University of Delaware, Newark, DE (US)

( * ) Notice: Subject to any disclaimer, the term of this patent is extended or adjusted under 35 U.S.C. 154(b) by 965 days.

(21) Appl. No.: 12/174,913

(22) Filed: Jul. 17, 2008

(65) Prior Publication Data

US 2009/0023916 A1   Jan. 22, 2009

Related U.S. Application Data

(60) Provisional application No. 60/959,803, filed on Jul. 17, 2007.

(51) Int. Cl.
*C07D 257/08*  (2006.01)
*C07D 243/10*  (2006.01)
*C07D 401/14*  (2006.01)
*C07D 401/04*  (2006.01)
*C07D 403/04*  (2006.01)
*C07D 403/14*  (2006.01)

(52) U.S. Cl. ......... 544/179; 544/234; 544/235; 544/238

(58) Field of Classification Search .................. 544/179, 544/234, 235, 238
See application file for complete search history.

(56) References Cited

U.S. PATENT DOCUMENTS

2010/0016545 A1   1/2010   Wiessler et al.

FOREIGN PATENT DOCUMENTS

EP   1867638   12/2007

OTHER PUBLICATIONS

Clavier et al. Chem. Rev. 2010, 110, 3299-3314.*
Muller et al., Synthesis 2006, No. 9, 1513-1517.*
Saracoglu, N. Tetrahedron 63 (2007) 4199-4236.*
Hamasaki, A. et al., J. Org. Chem. 2006, 71, 185-193.*
Baldwin, J. E.; Villarica, K. A.; "Syntheses of Two Stereoselectively Trideuterated Vinylcyclopropanes"; *J. Org. Chem.* 1995, 60, 186.
Kolb, H. C.; Finn, M. G.; Sharpless, K. B., "Click chemistry: Diverse chemical function from a few good reactions"; *Angew. Chem. Int. Edit.* 2001, 40, 2004.
Wang, Q.; Chan, T. R.; Hilgraf, R.; Fokin, V. V.; Sharpless, K. B.; Finn, M. G., "Bioconjugation by Copper(I)-Catalyzed Azide-Alkyne 3+2 Cycloaddition"; *J. Am. Chem. Soc.* 2003, 125, 3192.
Sen Gupta, S., et al.; "Accelerated bioorthogonal conjugation: A practical method for the Ligation of diverse functional molecules to a polyvalent virus scaffold"; *Bioconjugate Chemistry* 2005, 16, 1572.
Lewis, W. G.; Magallon, F. G.; Fokin, V. V.; Finn, M. G., "Discovery and characterization of catalysts for azide-alkyne cycloaddition by fluorescence quenching"; *J. Am. Chem. Soc.* 2004, 126, 9152.

Link, A. J.; Tirrell, D. A., "Cell surface labeling of *Eschericial coli* via copper (I) catalyzed 3+2 cycloaddition"; *J. Am. Chem. Soc.* 2003, 125, 11164.
Deiters, A.; Schultz, P. G., "In vivo incorporation of an alkyne into proteins in *Escherichia coli*"; *Bioorg. Med. Chem. Lett.* 2005, 15, 1521.
Antos, J. M.; Francis, M. B., "Transition metal catalyzed methods for site-selective protein modification"; *Curr. Opin. Chem. Biol.* 2006, 10, (3), 253.
Chen, I.; Ting, A. Y., "Site-specific labeling of proteins with small molecules in live cells"; *Curr. Opin. Biotech.* 2005, 16, 35.
Hahn, M. E.; Muir, T. W., "Manipulating proteins with chemistry: a cross-section of chemical biology"; *Trends in Biochemical Sciences* 2005, 30, (1), 26.
Kohn, M.; Breinbauer, R., "The Staudinger ligation—A gift to chemical biology"; *Angew. Chem. Int. Edit.* 2004, 43, 3106.
Tam, J. P.; Xu, J. X.; Eom, K. D., "Methods and strategies of peptide ligation"; *Biopolymers* 2001, 60, 194.
Dawson, P. E.; Muir, T. W.; Clark-Lewis, I.; Kent, S. B. H., "Synthesis of Proteins by Native Chemical Ligation"; *Science* 1994, 266, 776-779.
Muir, T. W., "Semisynthesis of proteins by expressed protein ligation"; *Annual Review of Biochemistry* 2003, 72, 249.
Muir, T. W., "Development and application of expressed protein ligation"; *Synlett* 2001, (6), 733.
Marcaurelle, L. A.; Bertozzi, C. R., "New directions in the synthesis of glycopeptide mimetics"; *Chem. Eur. J.* 1999, 5, 1384.
de Araujo, A. D., et al.; "Diels-Alder ligation and surface immobilization of proteins"; *Angew. Chem. Int. Edit.* 2006, 45, 296-301.
Latham-Timmons, H. A.; et al., "Novel method for the covalent immobilization of oligonucleotides via Diels-Alder bioconjugation"; *Nucleosides Nucleotides & Nucleic Acids* 2003, 22, 1495.
Houseman, B. T.; Mrksich, M., "Carbohydrate arrays for the evaluation of protein binding and enzymatic modification"; *Chemistry & Biology* 2002, 9, 443. Yousaf, M. N.; Houseman, B. T.; Mrksich, M., "Using electroactive substrates to pattern the attachment of two different cell populations"; *P.N.A.S. USA* 2001, 98, 5992.
Yousaf, M. N.; Mrksich, M., "Diels-Alder reaction for the selective immobilization of protein to electroactive self-assembled monolayers"; *J. Am. Chem. Soc.* 1999, 121, 4286.
Seelig, B.; Jaschke, A., "Site-specific modification of enzymatically synthesized RNA: Transcription initiation and Diels-Alder reaction"; *Tetrahedron Lett.* 1997, 38, 7729.
Marchan, V.; Ortega, S.; Pulido, D.; Pedroso, E.; Grandas, A., "Diels-Alder cycloadditions in water for the straightforward preparation of peptide-oligonucleotide conjugates"; *Nucleic Acids Research* 2006, 34, 3, pp. 1-9; article correction, 34, 5, p. 1668.
Hill, K. W, et al.; "Diels-Alder bioconjugation of diene-modified oligonucleotides"; *J. Org. Chem.* 2001, 66, 5352.

(Continued)

*Primary Examiner* — Venkataraman Balasubramanian
(74) *Attorney, Agent, or Firm* — RatnerPrestia

(57) ABSTRACT

Coupling reactions, suitable for use in organic or aqueous media, are performed by contacting a 1,2,4,5-tetrazine with a dienophile. The dienophile may be covalently bonded to a protein, and the coupling reaction may be performed in biological media such as those containing cells or cell lysates. The reactions may be performed in the presence of primary amines, thiols, acetylenes, azides, phosphines, and products of Staudinger and/or Sharpless-Huisgen reactions Novel 3-substituted cyclopropene compounds and trans-cyclooctenes are exemplary dienophiles for these reactions.

22 Claims, 3 Drawing Sheets

OTHER PUBLICATIONS

Tilley, S. D.; Francis, M. B., "Tyrosine-selective protein alkylation using pi-allylpalladium complexes"; *J. Am. Chem. Soc.* 2006, 128, 1080.

Antos, J. M.; Francis, M. B., "Selective tryptophan modification with rhodium carbenoids in aqueous solution"; *J. Am. Chem. Soc.* 2004, 126, (33), 10256.

Carrillo, N.; Davalos, E. A.; Russak, J. A.; Bode, J. W., "Iterative, Aqueous Synthesis of beta-oligopeptides without Coupling Reagent"; *J. Am. Chem. Soc.* 2006, 1452.

Bode, J. W.; Fox, R. M.; Baucom, K. D., "Decarboxylative Condensations of alpha-Ketoacids and N-Alkylhydroxylamines: A New Amide Ligation Reaction"; *Angew. Chem. Int. Ed.* 2006, 45, 1248.

Kolakowski, R. V.; Shangguan, N.; Sauers, R. R.; Williams, L. J., "Mechanism of thio acid/azide amidation"; *J. Am. Chem. Soc.* 2006, 128, 5695.

Galoni, D. P., et al.; "Aziridine-2-carboxylic Acid-Containing Peptides: Application to Solution- and Solid-Phase Convergent Site-Selective Peptide Modification"; *J. Am. Chem. Soc.* 2005, 127, 7359.

Saxon, E.; Bertozzi, C. R., "Cell surface engineering by a modified Staudinger reaction"; *Science* 2000, 287, (5460), 2007.

Nilsson, B. L.; Kiessling, L. L.; Raines, R. T., "Staudinger ligation: A peptide from a thioester and azide"; *Org. Lett.* 2000, 2, 1939.

Soellner, M. B.; Nilsson, B. L.; Raines, R. T., "Reaction mechanism and kinetics of the traceless Staudinger ligation"; *J. Am. Chem. Soc.* 2006, 128, 8820.

Soellner, M. B.; Dickson, K. A.; Nilsson, B. L.; Raines, R. T., "Site-specific protein immobilization by Staudinger ligation"; *J. Am. Chem. Soc.* 2003, 125, 11790.

Nilsson, B. L.; Hondal, R. J.; Soellner, M. B.; Raines, R. T., "Protein assembly by orthogonal chemical ligation methods"; *J. Am. Chem. Soc.* 2003, 125, 5268.

Nilsson, B. L.; Kiessling, L. L.; Raines, R. T., "High-yielding Staudinger ligation of a phosphinothioester and azide to form a peptide"; *Org. Lett.* 2001, 3, (1), 9-12.

Lin, F. L.; Hoyt, H. M.; van Halbeek, H.; Bergman, R. G.; Bertozzi, C. R., "Mechanistic investigation of the Staudinger ligation"; *J. Am. Chem. Soc.* 2005, 127, 2686.

Hang, H. C.; Yu, C.; Pratt, M. R.; Bertozzi, C. R., "Probing glycosyltransferase activities with the Staudinger ligation"; *J. Am. Chem. Soc.* 2004, 126, (1), 6.

Saxon, E., et al.; "Investigating cellular metabolism of synthetic azidosugars with the Staudinger ligation"; *J. Am. Chem. Soc.* 2002, 124, 14893.

Saxon, E.; Armstrong, J. I.; Bertozzi, C. R., "A "traceless" Staudinger ligation for the chemoselective synthesis of amide bonds"; *Org. Lett.* 2000, 2, 2141.

Prescher, J. A.; Bertozzi, C. R., "Chemistry in living systems"; *Nature Chemical Biology* 2005, 1, 13.

Prescher, J. A.; Dube, D. H.; Bertozzi, C. R., "Chemical remodelling of cell surfaces in living animals"; *Nature* 2004, 430, 873.

Deiters, A., et al.; "Adding amino acids with novel reactivity to the genetic code of *Saccharomyces cerevisiae*"; *J. Am. Chem. Soc.* 2003, 125, 11782.

Chin, J. W.; Santoro, S. W.; Martin, A. B.; King, D. S.; Wang, L.; Schultz, P. G., "Addition of p-azido-L-phenylalanine to the genetic code of *Escherichia coli*"; *J. Am. Chem. Soc.* 2002, 124, 9026.

Link, A. J.; Mock, M. L.; Tirrell, D. A., "Non-canonical amino acids in protein engineering"; *Curr. Opin. Biotech.* 2003, 14, 603.

Kiick, K. L.; Saxon, E.; Tirrell, D. A.; Bertozzi, C. R., "Incorporation of azides into recombinant proteins for chemoselective modification by the Staudinger ligation"; *P.N.A.S. USA* 2002, 99, 19.

Agard, N. J.; Prescher, J. A.; Bertozzi, C. R., "A strain-promoted [3+2] azide-alkyne cycloaddition for covalent modification of biomolecules in living systems"; *J. Am. Chem. Soc.* 2004, 126, (46), 15046.

Sauer, J., et al.; "[4+2] cycloadditions of 1,2,4,5-tetrazines and cyclopropenes—Synthesis of 3,4-diazanorcaradienes and tetracyclic aliphatic azo compounds"; *Eur. J. Org. Chem* 2001, (14), 2629.

Sauer, J., et al.; "The cycloaddition-cycloelimination pathway to homotropilidenes—Synthesis and properties of homotropilidenes"; *Eur. J. Org. Chem* 2001, 2639.

Thalhammer, F.; Wallfahrer, U.; Sauer, J., "Reactivity of Simple Open-Chain and Cyclic Dienophiles in Inverse-Type Diels-Alder Reactions"; *Tetrahedron Letters* 1990, 31, 6851.

Steigel, A., et al.; "Nitrogen Analogs of Cycloheptatrienes and Norcaradienes—Nuclear Magnetic-Resonance Study of Their Thermodynamic and Kinetic Properties"; *J. Am. Chem. Soc.* 1972, 94, 2770.

Hoogenboom, R.; Moore, B. C.; Schubert, U. S., "Synthesis of star-shaped poly(epsilon-caprolactone) via 'click' chemistry and 'supramolecular click' chemistry"; *Chemical Communications* 2006, 4010-4012.

Wijnen, J. W., et al.; "Substituent effects on an inverse electron demand hetero Diels-Alder reaction in aqueous solution and organic solvents: Cycloaddition of substituted styrenes to di(2-pyridyl)-1,2,4,5-tetrazine"; *J. Org. Chem.* 1996, 61, 2001.

Closs, G. L.; Boll, W. A.; Closs, L. E., "Base-Induced Pyrolysis of Tosylhydrazones of Alpha,Beta-Unsaturated Aldehydes and Ketones—a Convenient Synthesis of Some Alkylcyclopropenes"; *J. Am. Chem. Soc.* 1963, 85, 3796.

Braddock, D. C.; Cansell, G.; Hermitage, S. A.; White, A. J. P., "An asymmetric synthesis of enantiopure chair and twist trans-cyclooctene isomers"; *Tetrahedron-Asymmetry* 2004, 15, 3123.

Whitham, G. H.; Wright, M., "Trans-Cycloalkenes .1. (1RS,2RS)-Trans-Cyclo-Oct-2-En-1-ol"; *J. Chem. Soc. (C)* 1971, 883.

Whitham, G. H.; Wright, M., "Trans-Cycloalkenes .2. Application of Dioxolan Olefin Synthesis to Stereospecific Formation of Trans-Cyclo-Octene Derivatives—(1RS,2RS)-Trans-Cyclo-Oct-2-En-1-Ol"; *J. Chem. Soc. (C)* 1971, 886.

Whitham, G. H.; Wright, M.; "Trans-Cycloalkenes .3. Stereochemistry and Mechanism of Some Reactions of Diastereoisomeric 3-Substituted Trans-Cyclo-Octenes"; *J. Chem. Soc. (C)* 1971, 891.

Loozen, H. J. J., et al.; "Silver Ion Assisted Ring Expansions of Some Geminal Dibromobicyclo[n.1.0]Alkanes—Evidence for Free Cationic Intermediates"; *J. Org. Chem.* 1977, 42, 418.

Wells, A. P.; Riches, B. H.; Kitching, W.; "Electrophile Induced Reactions of Medium Ring Vinyl-Silanes and 1,2-Epoxy-Silanes and Related-Compounds"; *J. Chem. Soc., Chem. Commun.* 1992, 1575.

Tsuneishi, H.; Inoue, Y.; Hakushi, T.; Tai, A.; "Direct and Sensitized Geometrical Photoisomerization of 1-Methylcyclooctene"; *Journal of the Chemical Society-Perkin Transactions 2* 1993, 457.

Vedejs, E.; Snoble, K. A. J.; Fuchs, P. L.; "Phosphorus Betaines Derived from Cycloheptene and Cyclooctene Oxides—Inversion of Cyclooctenes"; *J. Org. Chem.* 1973, 38, 1178.

Corey, E. J.; Carey, F. A.; Winter, R. A. E., "Stereospecific Syntheses of Olefins from 1,2-Thionocarbonates and 1,2-Trithiocarbonates . Trans-Cycloheptene"; *J. Am. Chem. Soc.* 1965, 87, 934.

Cope, A. C.; Pike, R. A.; Spencer, C. F., "Cyclic Polyolefins XXVII. Cis-Cyclooctene and Trans-Cyclooctene from N,N-Dimethylcyclooctylamine"; *J. Am. Chem. Soc.* 1953, 75, 3212.

Hines, J. N., et al.; "Some Reactions of Benzaldehyde Acetals with Alkyl-Lithium Reagents—Stereospecific Olefin Synthesis from 1,2-Diols"; *J. Chem. Soc., Perkin Trans 1* 1973, 2332.

Inoue, T., et al.; "Diastereodifferentiating Z-E photoisomerization of 3-benzoyloxycyclooctene: Diastereoselectivity switching controlled by substrate concentration through competitive intra- vs intermolecular photosensitization processes"; *J. Am. Chem. Soc.* 1999, 121, 9877.

Shi, M.; Inoue, Y.; "Geometrical photoisomerization of (Z)-cyclooctene sensitized by aromatic phosphate, phosphonate, phosphinate, phosphine oxide and chiral phosphoryl esters"; *Journal of the Chemical Society-Perkin Transactions 2* 1998, 2421.

Inoue, Y.; Matsushima, E.; Wada, T.; "Pressure and temperature control of product chirality in asymmetric photochemistry. Enantiodifferentiating photoisomerization of cyclooctene sensitized by chiral benzenepolycarboxylates"; *J. Am. Chem. Soc.* 1998, 120, 10687.

Inoue, Y.; Yamasaki, N.; Yokoyama, T.; Tai, A.; "Highly Enantiodifferentiating Photoisomerization of Cyclooctene by Congested and or Triplex-Forming Chiral Sensitizers"; *J. Org. Chem.* 1993, 58, 1011.

Yamasaki, N.; Inoue, Y.; Yokoyama, T.; Tai, A.; "High Photostationary State Trans Cis Ratios Upon Aromatic Ester-Sensitized Photoisomerization of Cyclooctene"; *J. Photochem. Photobiol. A—Chemistry* 1989, 48, 465.

Inoue, Y.; Takamuku, S.; Sakurai, H.; "Anomalously High Trans-Cis Photostationary Ratio on Direct Photoisomerization of Cyclo-Octene"; *J. Chem. Soc., Chem. Commun.* 1976, (11), 423.

Deyrup, J. A.; Betkousk M.; "Alkene Isomerization—Improved One-Step Synthesis of Trans Cyclooctene"; *J. Org. Chem.* 1972, 37, 3561.

Cope, A. C.; Bach, R. D.; "trans-Cyclooctene"; *Org. Synth. Coll. vol.* *5* 1973, 315.

* cited by examiner

TETRAZINE-BASED BIO-ORTHOGONAL COUPLING REAGENTS AND METHODS

CROSS REFERENCE TO RELATED APPLICATIONS

This application claims priority benefit of U.S. Provisional Patent Application No. 60/959,803, filed Jul. 17, 2007, the entirely of which is incorporated herein by reference.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. GM068640-01, awarded by the National Institutes of Health.

BACKGROUND OF THE INVENTION

Reactions that are selective and orthogonal to (i.e., non-interacting with) the functionality found in biological systems are broadly useful tools with applications that span synthesis, chemical biology, and materials science. However, despite being grounded in some of the most venerable name reactions in organic synthesis, the development of reaction types that can selectively interface with biological molecules is a recent advance and continuing challenge. Examples of such bio-orthogonal coupling reactions include Native Chemical Ligation (NCL) and Expressed Protein Ligation (EPL), carbonyl ligations, Diels-Alder reactions, Pd— and Rh-catalyzed ligations, decarboxylative condensations, thio-acid/azide ligations, aziridine ligations, the Staudinger ligation, and the Sharpless-Huisgen cycloaddition. The latter two reactions, both of which involve reactivity of azides, are shown below.

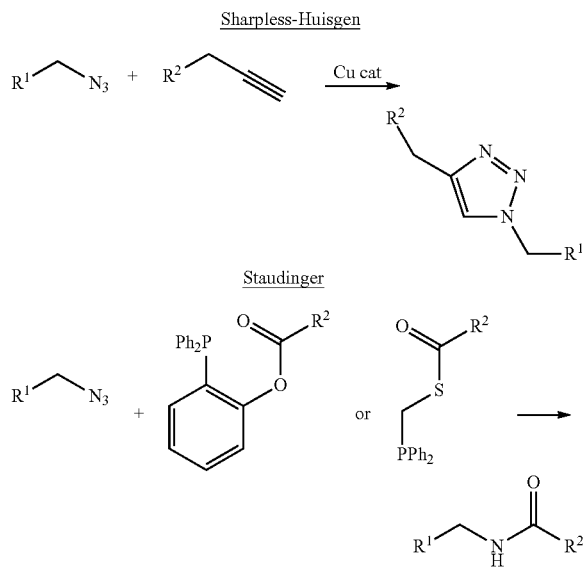

These reactions are often cited as examples of 'click chemistry,' a term used in the art to refer to chemical reactions that are specific, high yielding, and tolerant of functional groups. Click reactions do not generate significant byproducts (or only inoffensive byproducts), and can take place in a variety of reaction media, including water. Such reactions are orthogonal to most of the functional groups found in biological systems, and accordingly click chemistry has become a broadly useful tool for chemical biology and materials science.

The high selectivity and broad compatibility of these reactions are manifested in a variety of reaction environments, even in living cells. Furthermore, it has proven possible to express proteins that incorporate either alkynes or azides, providing a handle for protein ligation.

Despite the above advantages, these reactions are not without drawbacks. These include the cytotoxicity of the copper catalyst in the Sharpless-Huisgen reaction with simple alkynes and competing phosphine oxidation for the Staudinger reaction. Furthermore, the reaction rates are often slow, and therefore require high concentrations and/or a large excess of one reactant. This is impractical for many applications.

A further challenge for the field has been to develop new coupling reactions that are orthogonal to these existing chemistries, as well as to the functional groups typically found in biological systems. Providing such additional bio-orthogonal coupling chemistries would be very desirable as a next step in building a toolkit for preparing complex, multidomain biological structures.

The Diels-Alder reaction is one possible candidate for providing a reaction sequence that is orthogonal to the functional groups used in the above reactions as well as those typically found in biological systems. Diels-Alder reactions employing maleimide derivatives as dienophiles have been used in bioconjugation reactions of oligonucleotides, carbohydrates, and peptides. Such reactions have been used to immobilize biological molecules onto surfaces, and as a coupling tool for proteins. However, maleimide-based Diels-Alder couplings suffer from two major limitations: relatively slow reaction rates, and the incompatibility with free thiols. Thus, high concentrations (>1 mM) are typically required for the bioconjugations of diene-modified oligonucleotides (2-24 h at 37° C.). A more severe limitation is that free thiols react with maleimide via conjugate addition. As one solution, Waldmann has shown that Ellman's reagent can be used to protect the thiol groups in the surface cysteines of Rab7. However, a method that tolerates thiols would obviate the need for such a step, and would be a very desirable advance.

One possible way of addressing the problem of thiol-reactivity of the dienophile might be to use a different kind of dienophile/diene combination. One possible such combination would be an Inverse Electron Demand Diels-Alder (IED-DA) pair of reactants. For example, 1,2,4,5-tetrazine derivatives are well known as powerful dienes in inverse electron demand Diels-Alder (IED-DA) reactions of alkenes and alkynes. Such reactions of 1,2,4,5-tetrazines are typically followed by a retro-Diels-Alder reaction to expel nitrogen. Strained alkenes are particularly reactive in (IED-DA) reactions, and the kinetics of IED-DA reactions of strained molecules with 1,2,4,5-tetrazine derivatives 1a and 1b have been elucidated by J. Sauer as shown below.

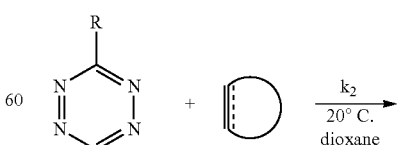

1a: R = CO₂Me
1b: R = CF₃

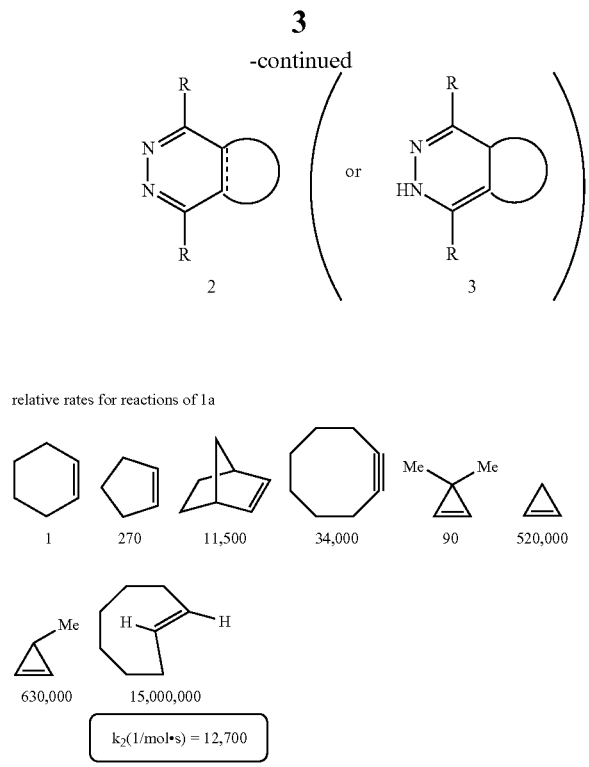

relative rates for reactions of 1a $k_2(1/mol \cdot s) = 12,700$

All of these reactions initially produce structures 2. For certain dienophiles (e.g., trans-cyclooctene) the initially formed product 2 tautomerizes to 3. Remarkably, the rates with various dienophiles span 7 orders of magnitude. In particular, trans-cyclooctene, cyclopropene, and 3-methylcyclopropene display high reactivity.

Unfortunately, although IED-DA reactions involving 1,2,4,5-tetrazines can be very rapid, such reactions using known 1,2,4,5-tetrazines have some particularly troublesome shortcomings relative to their potential use in many applications, especially in aqueous systems such as biological media. For example, dienes 1a and 1b are themselves reactive toward water. Other tetrazines, such as 3,6-di-(2-pyridyl)-1,2,4,5-tetrazine (4), are more stable to aqueous conditions but react only slowly in water with dienophiles such as styrenes, making such reactions impractical in many applications. Further, the reactions of 4 had not been demonstrated in the presence of biological molecules or media (e.g., cellular lysate or cell culture media).

Scheme 1 Reported rate of the reaction of 4 with styrene in water

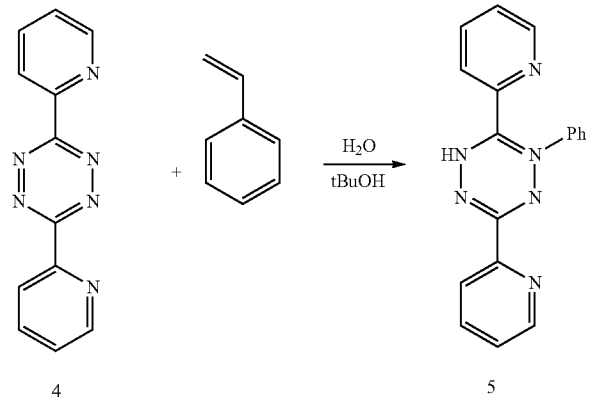

$k_2 (1/mol \cdot s) = 0.13$

On the other hand, while cyclopropene and trans-cyclooctene have been known to display exceptional reactivity toward tetrazines in IED-DA chemistry, the synthesis of suitable derivatives has been a serious limitation. For cyclopropenes, fast reactivity has typically been found only for those compounds bearing a single substituent at C-3. For example, as shown above, the reaction of a tetrazine with 3-methylcyclopropene is ~7000 faster than the analogous reaction with 3,3-dimethylcyclopropene. However, cyclopropenes with a single C-3 substituent have typically been too reactive to be stored, much less used in bioconjugation. For example, 3-methylcyclopropene is too reactive to be stored as a neat material, and is generally used immediately upon generation.

As seen above, trans-cyclooctene is a remarkably reactive dienophile in IED-DA reactions. However, although there are a number of preparations of the parent compound, syntheses of substituted trans-cyclooctenes are relatively few. Typically, trans-cyclooctenes are prepared via several chemical steps from the analogous cis-cyclooctene (or a more expensive/complex precursor). Far superior would be a direct synthesis of the trans- from the cis-isomer. Efforts have been made to achieve this through sensitized photolysis, but unfortunately such photochemical syntheses have typically been not preparatively useful because high dilution has been required, and because photolysis produces a mixture of cis- and trans-cyclooctene that needs to be separated by washing the mixture with aqueous $AgNO_3$ (only the trans-isomer coordinates strongly to $AgNO_3$, forming a water-soluble complex).

Perhaps due to the above-mentioned impediments, the inventors are unaware of any known, practically useful Diels-Alder based chemistries that are tolerant of aqueous environments, tolerant of thiol and amine groups, and of sufficient reaction rate as to have broad utility in biological systems.

SUMMARY OF THE INVENTION

In one aspect, the invention provides a method of performing a coupling reaction, including contacting a 1,2,4,5-tetrazine with a dienophile in an organic or aqueous medium including at least one species selected from the group consisting of primary amines, thiols, Staudinger reactants, Staudinger adducts, Sharpless-Huisgen reactants, and Sharpless-Huisgen adducts. The contacting is performed under conditions sufficient to convert at least 50% of the 1,2,4,5-tetrazine or the dienophile to a Diels-Alder adduct of the 1,2,4,5-tetrazine with the dienophile.

In another aspect, the invention provides a method of performing a coupling reaction, including contacting a 1,2,4,5-tetrazine with a dienophile in an organic or aqueous medium. The contacting is performed under conditions sufficient to convert at least 50% of the 1,2,4,5-tetrazine or the dienophile to a Diels-Alder adduct of the 1,2,4,5-tetrazine with the dienophile, wherein the dienophile is covalently bonded to a protein.

In another aspect, the invention provides a method of performing a coupling reaction that includes contacting a 1,2,4,5-tetrazine selected from the group consisting of compounds according to formulas (4), (22), (23), (30), (31), (32), (33) and (34)

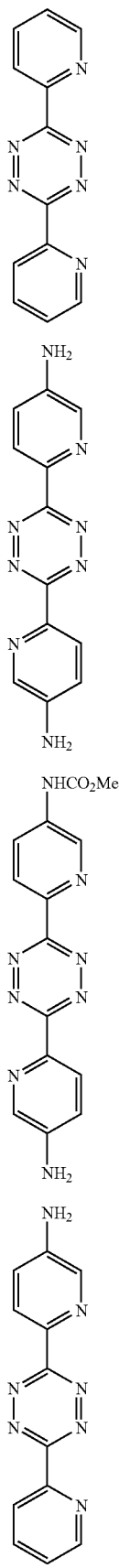
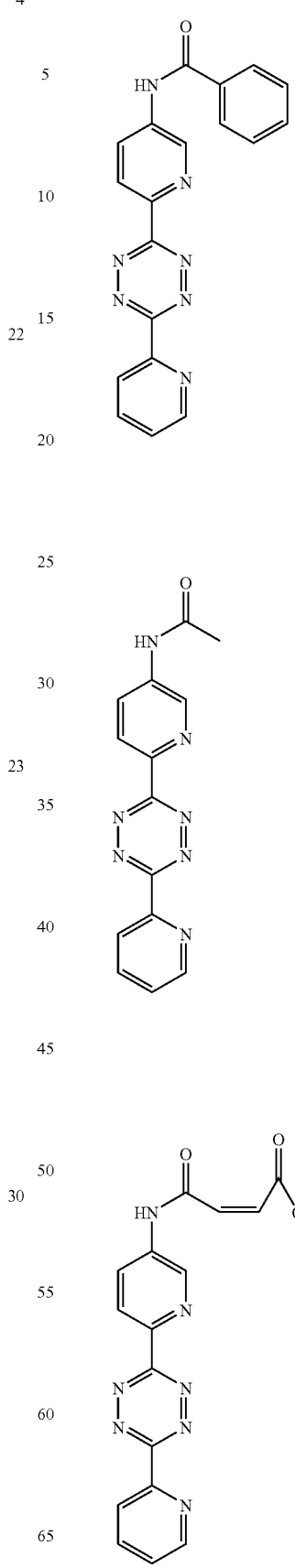

34

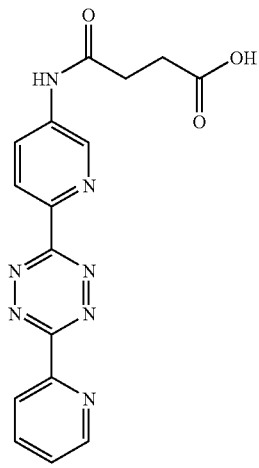

with a substituted cyclopropene selected from the group consisting of compounds according to formulas (7), (8) and (27)

7

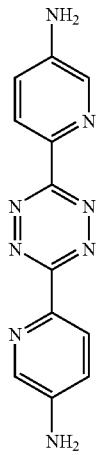

8

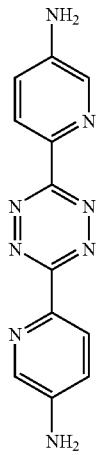

27

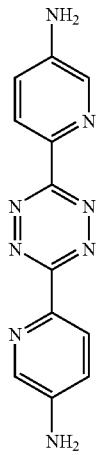

in an organic or aqueous medium under conditions sufficient to convert at least 50% of the 1,2,4,5-tetrazine or the substituted cyclopropene to a Diels-Alder adduct of the 1,2,4,5-tetrazine with the substituted cyclopropene.

In another aspect, the invention provides a method of performing a coupling reaction that includes contacting a 1,2,4,5-tetrazine selected from the group consisting of compounds according to formulas (4), (22), (23), (30), (31), (32), (33) and (34)

4

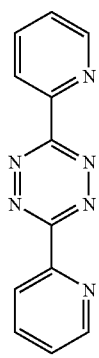

22

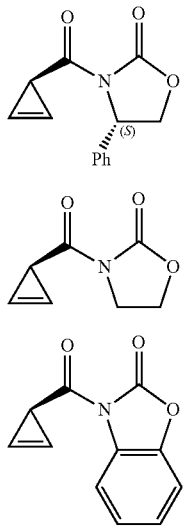

23

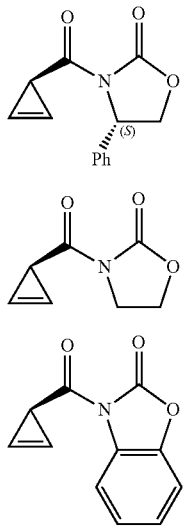

30

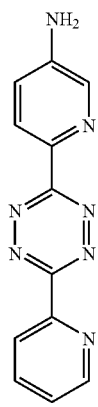

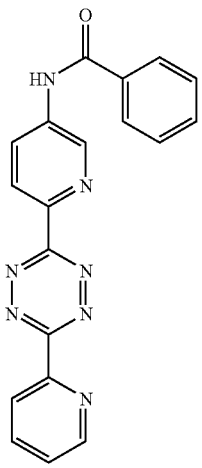

31

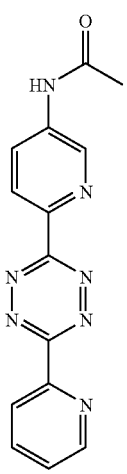

32

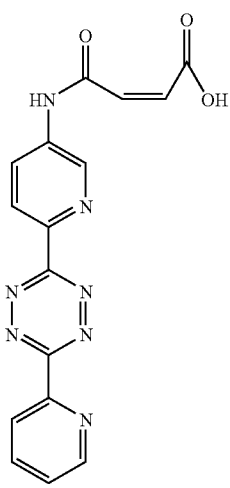

33

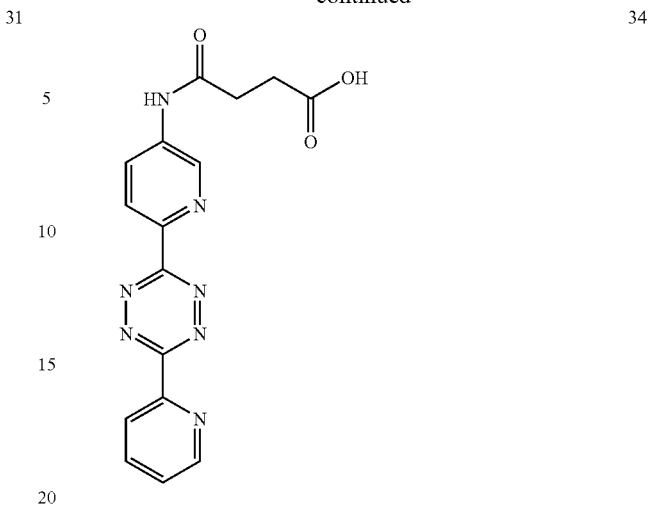

34 with trans-cyclooctene or a substituted trans-cyclooctene in an organic or aqueous medium under conditions sufficient to convert at least 50% of the 1,2,4,5-tetrazine, the trans-cyclooctene, or the substituted trans-cyclooctene to a Diels-Alder adduct of the 1,2,4,5-tetrazine with the trans-cyclooctene or the substituted trans-cyclooctene.

In another aspect, the invention provides a method of preparing a substituted or unsubstituted trans-cyclooctene. The method includes the steps of (a) exposing a solution of the cis-isomer of the substituted or unsubstituted trans-cyclooctene to ultraviolet radiation, thereby forming a solution including the substituted or unsubstituted trans-cyclooctene;

(b) contacting the solution formed in step (a) with $AgNO_3$ supported on a stationary phase, thereby binding at least a portion of the substituted or unsubstituted trans-cyclooctene to the stationary phase and producing a solution including the cis-isomer and a reduced amount of the substituted or unsubstituted trans-cyclooctene; and (c) freeing the substituted or unsubstituted trans-cyclooctene from the stationary phase.

In another aspect, the invention provides a method of preparing cycloprop-2-enecarboxylic acid that include the steps of (a) contacting a mixture including ethyl diazoacetate with acetylene in the presence of a rhodium catalyst to form an intermediate mixture;

(b) contacting the intermediate mixture with an alkali metal hydroxide to form an alkali metal salt of cycloprop-2-enecarboxylic acid; and (c) contacting the alkali metal salt with a strong acid to form cycloprop-2-enecarboxylic acid.

In another aspect, the invention provides a method of preparing a compound according to formula (7)

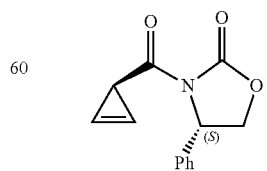

7 that includes contacting cycloprop-2-enecarboxylic acid with triethylamine and either pivaloyl chloride or 1-adamantyl chloride, and subsequently contacting the resulting mixture with lithium chloride, phenyloxazolidinone and 4-dimethylamino pyridine.

In another aspect, the invention provides a method of preparing a compound according to formula (8)

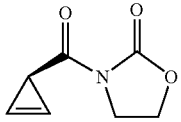
8 that includes contacting cycloprop-2-enecarboxylic acid with triethylamine and either pivaloyl chloride or 1-adamantyl chloride, and subsequently contacting the resulting mixture with lithium chloride, oxazolidinone and 4-dimethylamino pyridine.

In another aspect, the invention provides a method of preparing a compound according to formula (27)

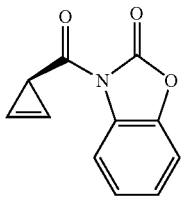
27 that includes contacting cycloprop-2-enecarboxylic acid with triethylamine and either pivaloyl chloride or 1-adamantyl chloride, and subsequently contacting the resulting mixture with lithium chloride, 2-benzoxazolinone and 4-dimethylamino pyridine.

In another aspect, the invention provides a 1,2,4,5-tetrazine selected from the group consisting of compounds according to formulas (4), (22), (23), (30), (31), (32), (33) and (34)

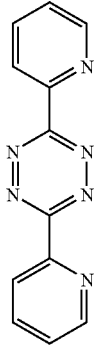
4

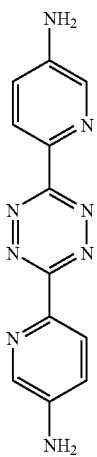
22

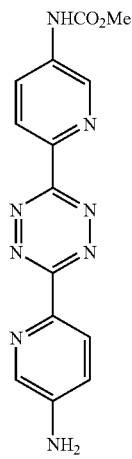
23

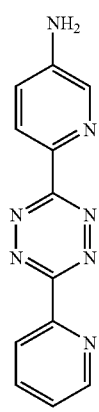
30

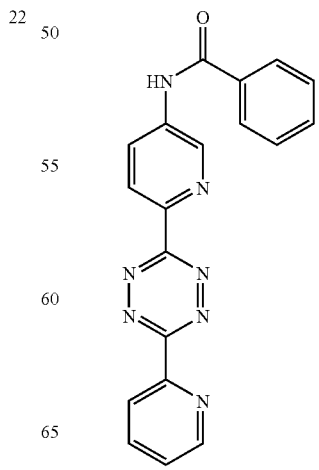
31

-continued
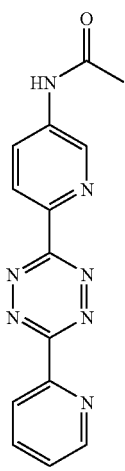
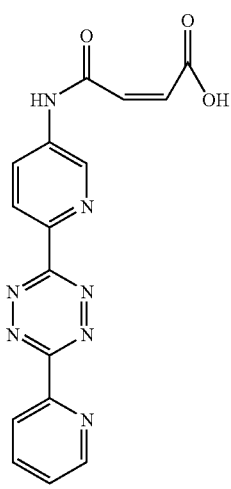
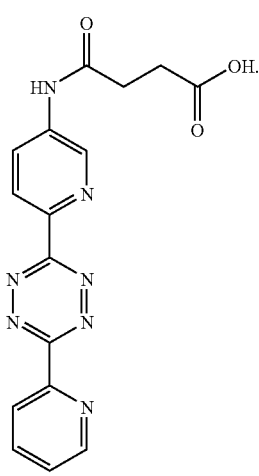
In another aspect, the invention provides a 3-substituted cyclopropene selected from the following compounds
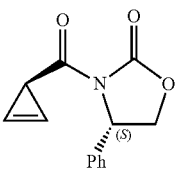
7
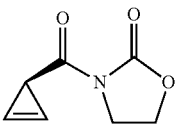
8
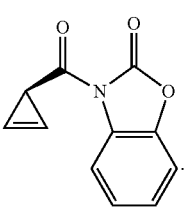
27
In another aspect, the invention provides a trans-cyclooctene selected from the following compounds
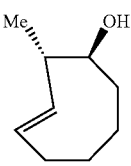
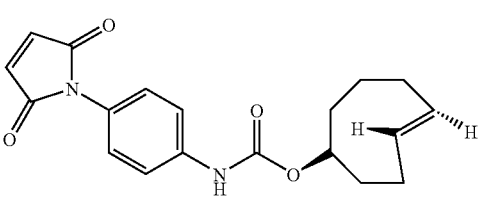
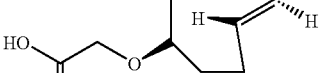

-continued

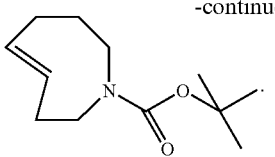

In another aspect, the invention provides a method of quantitative analysis including the steps of exposing an adduct of a 1,2,4,5-tetrazine with a dienophile to UV radiation, and measuring either the fluorescent emission or UV absorption of the sample.

DETAILED DESCRIPTION OF THE INVENTION

Figure 1:
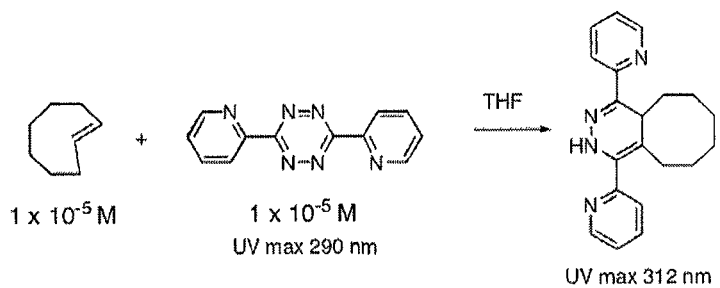
FIG. 1 shows ultraviolet absorption spectra taken at various times after mixing a 1,2,4,5-tetrazine and a dienophile according to the invention.
Figure 1:
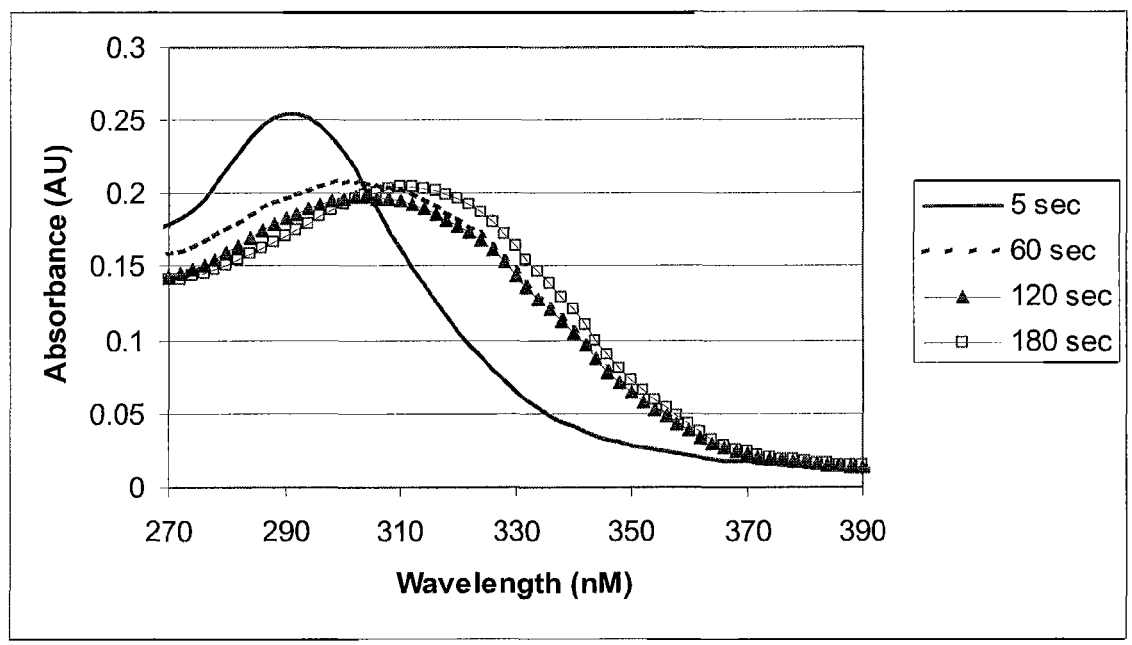

The inventors now disclose a new class of bio-orthogonal coupling reaction that proceeds with exceptionally high reaction rates, involving the Diels-Alder cycloaddition of 1,2,4,5-tetrazine derivatives with dienophiles. Two exemplary classes of dienophile, 3-substituted cyclopropenes and trans-cyclooctenes, are described in detail further below. The reaction tolerates a broad range of functionality, including thiols and primary amines, and the reaction proceeds in high yield in organic and aqueous media. As used herein, the term "aqueous media" means compositions including a solvent at least 50 wt % of which is water, and "organic media" are those in which there is no solvent or the solvent is at least 50% organic. Nonlimiting examples of organic solvents include ethanol, methanol, glycerol, and ethylene glycol, diethyl ether, toluene, benzene, hexane, ethyl acetate, THF, chloroform and methylene chloride. The reactions are typically suitable for use in cell culture media and in cell lysate. Indeed, the selectivity and aqueous compatibility of the reactions make them suitable for numerous in vivo and in vitro applications, including coupling reactions of small molecules, peptides, proteins, oligonucleotides, other types of polymers, nanoparticles, and on surfaces (e.g., glass slides, gold). Reactions of dienophiles with 1,2,4,5-tetrazine derivatives according to the invention are very rapid and selective The reactions are typically performed at a temperature no greater than 100° C., more typically no greater than 50° C., and even more typically no greater than 35° C. In most cases, the reaction is performed at ambient temperature. The concentration of the tetrazine or the dienophile (or both) in the reaction mixture is typically at most 0.1M, more typically at most 0.01M, and in some cases at most 0.001M. Typical times needed to complete the reaction are at most 5 hours, more typically at most 3 hours, and most typically at most 1 hour. In some embodiments, the reaction is complete in at most 30 minutes. The reaction converts at least 50% of the 1,2,4,5-tetrazine or the dienophile to a Diels-Alder adduct of the 1,2,4,5-tetrazine with the dienophile. Typically, the conversion is at least 90%, and more typically it is at least 95%. Usually, substantially all of at least one of the reactants is converted to the desired adduct. Due to the very high selectivity and speed of the reaction, the dienophile and the 1,2,4,5-tetrazine are typically used in approximately equimolar amounts. Thus, in some embodiments, the molar excess of one over the other is at most 50%, more typically at most 20%, and even more typically at most 10%. In many cases, equimolar amounts are used.

The reactions may be performed in the presence of amines (even primary amines) and/or thiols, including for example such moieties residing on amino acid groups, either free or incorporated in proteins or other biological species. The reactions may also be performed in the presence of Sharpless-Huisgen reactants, Staudinger reactants, and the adducts produced by these reactions. As used herein, the term "Sharpless-Huisgen reactant" refers to either an acetylene or an organic azide suitable for use in the Sharpless-Huisgen reaction. Each of these may be referred to as a "complementary" reactant with respect to the other, and the product of their reaction will be referred to as a "Sharpless-Huisgen adduct." Similarly, the term "Staudinger reactant" refers to either an azide or a phosphine (complementary reactants) suitable for use in the Staudinger reaction, and a Staudinger adduct is the product of such a reaction. As can be seen above, azides are Staudinger reactants as well as Sharpless-Huisgen reactants.

For purposes of this invention, and unless otherwise indicated, reference to a "Diels-Alder adduct" will be understood to include the directly formed adduct, the product of a subsequent retro-Diels-Alder reaction to expel nitrogen, or a tautomeric form of either of these. The preparation of certain trans-cyclooctenes and 3-substituted cyclopropenes, as well as certain 1,2,4,5-tetrazines, will now be described. Thereafter, experiments demonstrating the use of these materials according to the invention will be disclosed.

3-Substituted Cyclopropenes

The inventors have found that cyclopropene carboxylic acid derivatives 7 and 8, shown below in Scheme 2, are stable both as crystalline solids and in solution. For example, compound 7 is stable for at least one year in crystalline form, and decomposes only slowly (>12 h) when heated at 80° C. in DMSO. The inventors have developed preparations of these compounds suitable for large scale operation, using inexpensive ethyl diazoacetate and acetylene gas. These oxazolidinone derivatives are the only cyclopropenes with a single C-3 substituent known to the inventors to display long term stability. For example, the inventors have observed that cycloprop-2-enecarboxylic acid 6 decomposes within days at room temperature, and 3-methyl cycloprop-1-ene has been reported to be too unstable to handle at room temperature. The inventors have developed a synthesis of 6 and oxazolidinones of structure 7 and 8 that can be carried out on large scale, as shown in Scheme 2.

Scheme 2
Scalable synthesis of stable cyclopropenes for Diels-Alder ligation.

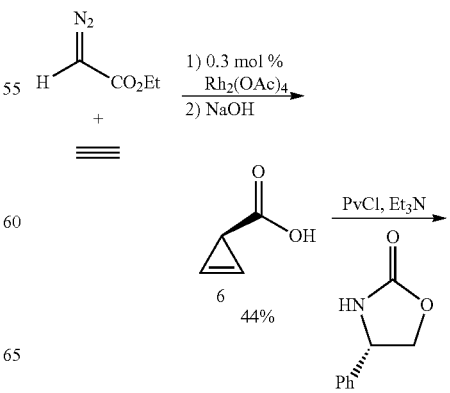

-continued

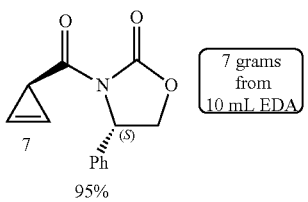

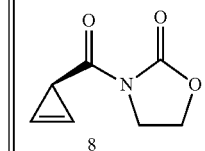

similar prep:
7 grams from 10 mL EDA

The method of forming 6 includes the steps of
(a) contacting a mixture comprising ethyl diazoacetate with acetylene in the presence of a rhodium catalyst to form an intermediate mixture;
(b) contacting the intermediate mixture with an alkali metal hydroxide to form an alkali metal salt of cycloprop-2-enecarboxylic acid; and
(c) contacting the alkali metal salt with a strong acid to form cycloprop-2-enecarboxylic acid.

Compounds 7 and 8 may be made by contacting cycloprop-2-enecarboxylic acid with triethylamine and either pivaloyl chloride or 1-adamantyl chloride, and subsequently contacting the resulting mixture with lithium chloride, 4-dimethylamino pyridine, and either phenyloxazolidinone or oxazolidinone, respectively. The analogous compound 27, shown below, can be made by a similar process. Like 7 and 8, compound 27 exhibits excellent stability.

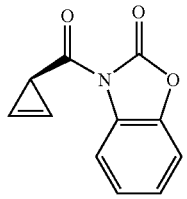

Functionalized Trans-Cyclooctenes

The inventors have also found that trans-cyclooctenes may be conveniently prepared by a practical photochemical procedure, one embodiment of which is shown in the Examples. In this method, the corresponding cis-cyclooctene is irradiated with ultraviolet light, optionally in the presence of a photosensitizer, to cause cis-trans isomerization. During the photoreaction, the reaction mixture is continuously pumped through an AgNO$_3$ impregnated silica gel stationary phase column. The trans-cyclooctene selectively binds to the column, and the cis-isomer returns to the reaction mixture, where it is again photolyzed. When cyclooctene is no longer present in the reaction mixture (GC analysis), the silica is removed and stirred with NH$_4$OH (decomplexes Ag), and the trans-cyclooctene recovered by extraction. The procedure is preparatively useful: the reactions can be carried out on gram scale in a modest amount of solvent (500 mL). However, without the AgNO$_3$ impregnated silica column, only trace amounts (<5%) of trans-cyclooctene derivatives are obtained in such procedures. The process may alternatively be performed in a stepwise manner with discrete irradiation steps and binding steps, rather than using a continuous pump-around of reaction mixture. A list of trans-cyclooctene derivatives that have been prepared by this procedure is displayed in Table 1.

Figure 3:
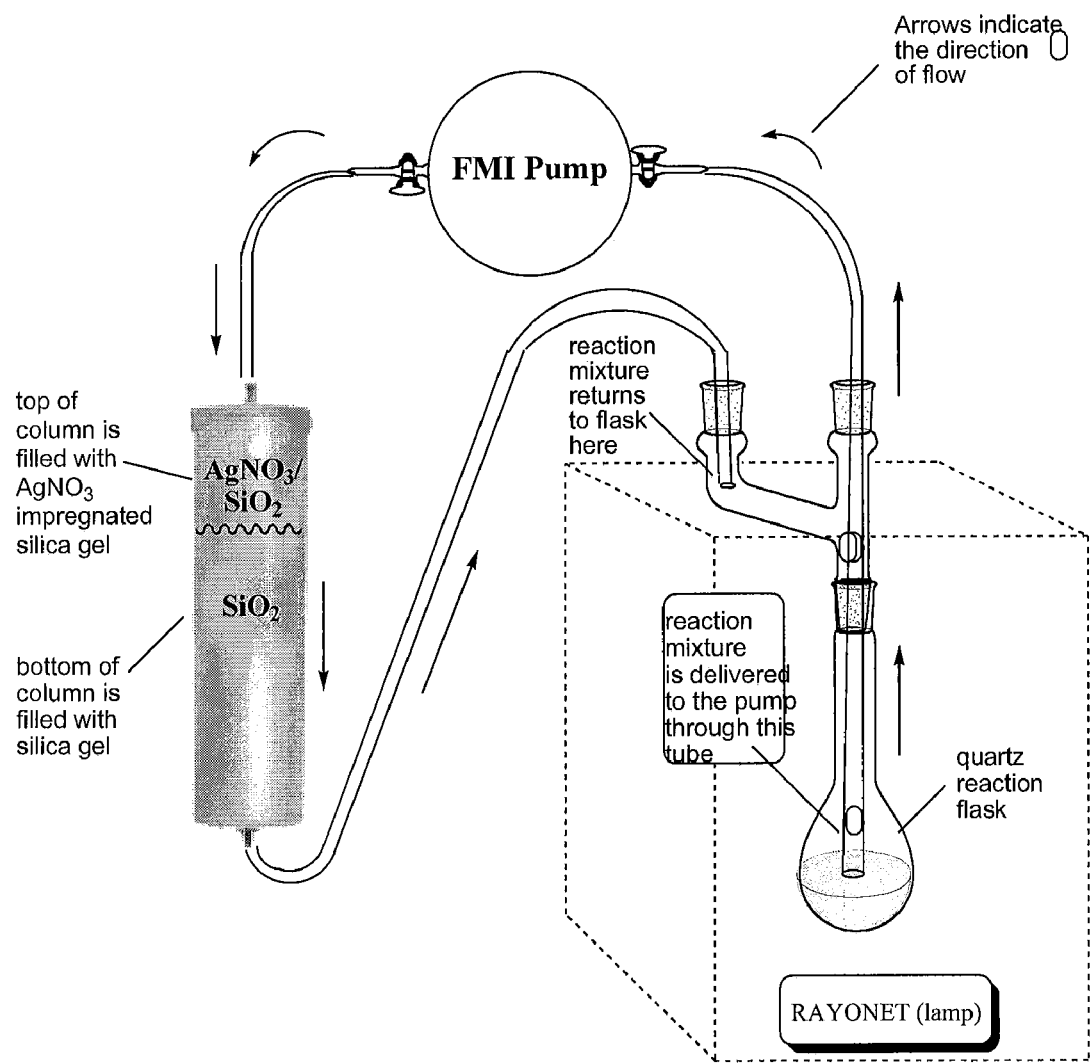
FIG. 3 shows an exemplary apparatus for preparing trans-cyclooctenes according to the invention.

TABLE 1 trans-cyclooctene derivatives prepared using the method described in FIG. 3.

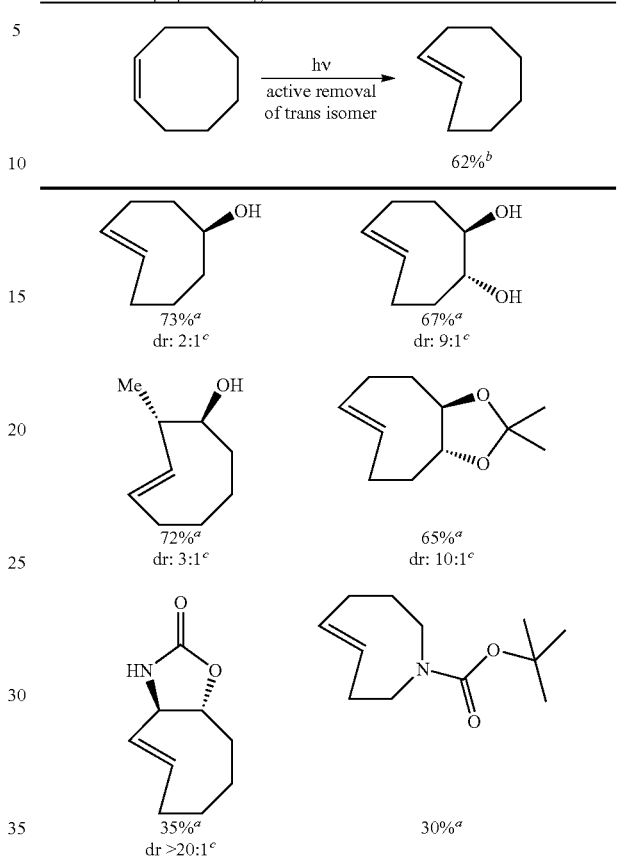

[a] isolated yield.
[b] yield determined by GC.
[c] only the major diastereomer is shown The Diels-Alder reactions of trans-cyclooctenes and substituted cyclopropenes such as those discussed above will now be described.

Inverse Electron Demand Diels-Alder Studies with Cyclopropenes

The inventors have studied the IED-DA reactions that form adducts 11 from cyclopropenes 7 and 8 and commercially available tetrazine 4 (Scheme 3). Several aspects are notable:

1) the yields of the reactions are high (>95%).
2) the reactions are fast enough to be useful for many biological applications (for 7+4, k~0.2 l/s·mol at 37° C.). The reactions are at least an order of magnitude faster than reported Diels-Alder reactions based on maleimide, and also faster than the CuSO$_4$ catalyzed Sharpless-Huisgen reaction of phenylacetylene with benzyl azide, and the Staudinger ligation.
3) the IED-DA reaction can be carried out in many solvents, including water
4) The IED-DA reaction displays orthogonal reactivity toward functional groups used in Sharpless-Huisgen reactions and in Staudinger reactions. For example, adduct 11 was formed cleanly even when 7 and 4 were reacted in THF in the presence of equimolar amounts of phenylacetylene and benzyl azide (Sharpless-Huisgen reactants) or in the presence of PPh$_3$ (Staudinger reactant), n-BuNH$_2$ or EtSH.

Scheme 3. Inverse electron demand Diels-Alder reactions of cyclopropenes.

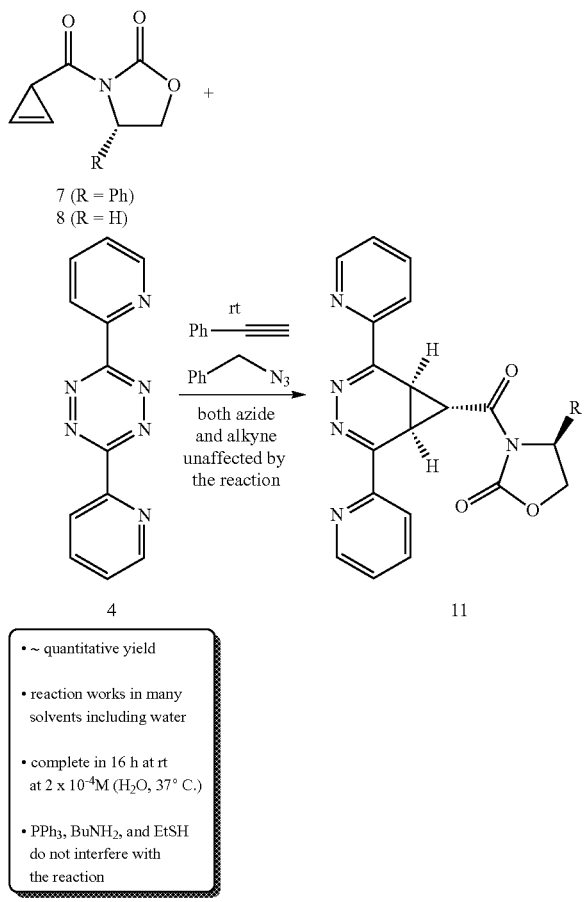

Inverse Electron Demand Diels-Alder Studies with Trans-Cyclooctene

The inventors have also studied the efficacy of trans-cyclooctene 12 in IED-DA chemistry with diene 4 (Scheme 4), and have found that the reactivity of this combination is remarkable. The reaction to form 13 is complete within 40 min at 25° C. at $5 \times 10^{-6}$ M without using an excess of either reagent. Phenylacetylene (a Sharpless-Huisgen substrate) does not react with either 4 or 12 under these conditions.

Scheme 4. Fast reactivity at micromolar concentration

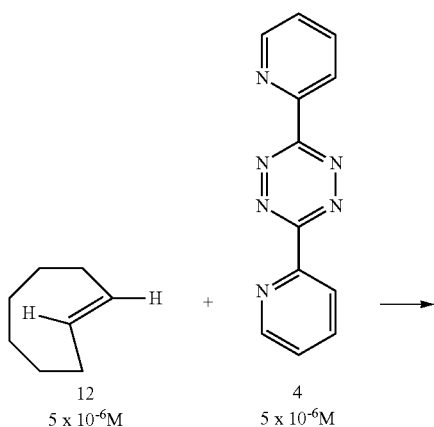

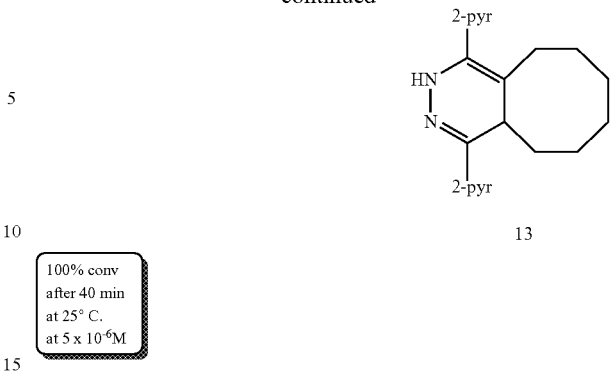

Absorption and Fluorescence Spectroscopy

Beyond the exceptional reaction rates, another advantage of the disclosed methods and compositions chemistry is that the starting materials and products of the tetrazine bio-orthogonal coupling are chromophores and fluorophores. Tetrazine 4 and trans-cyclooctene/tetrazine adduct 13 have distinctly different UV-Vis spectra, as shown as in FIG. 1, where the curve recorded after only 5 seconds of reaction time is the absorption curve of 4 and the one at 180 seconds reaction time is that of adduct 13. Tetrazine 4 has an absorption maximum at 290 nm, whereas the adduct 13 has an absorption maximum at 312 nm. At 360 nm, the tetrazine 4 is virtually non-absorbing. This provides a unique absorption signal that can be used as a label and as a probe for monitoring the progress of bio-orthogonal coupling reactions. Furthermore, as most proteins and many other biological molecules do not display absorption between 320-360 nm, the chromophore 13 can serve as a quantitative marker of protein coupling.

Figure 2:
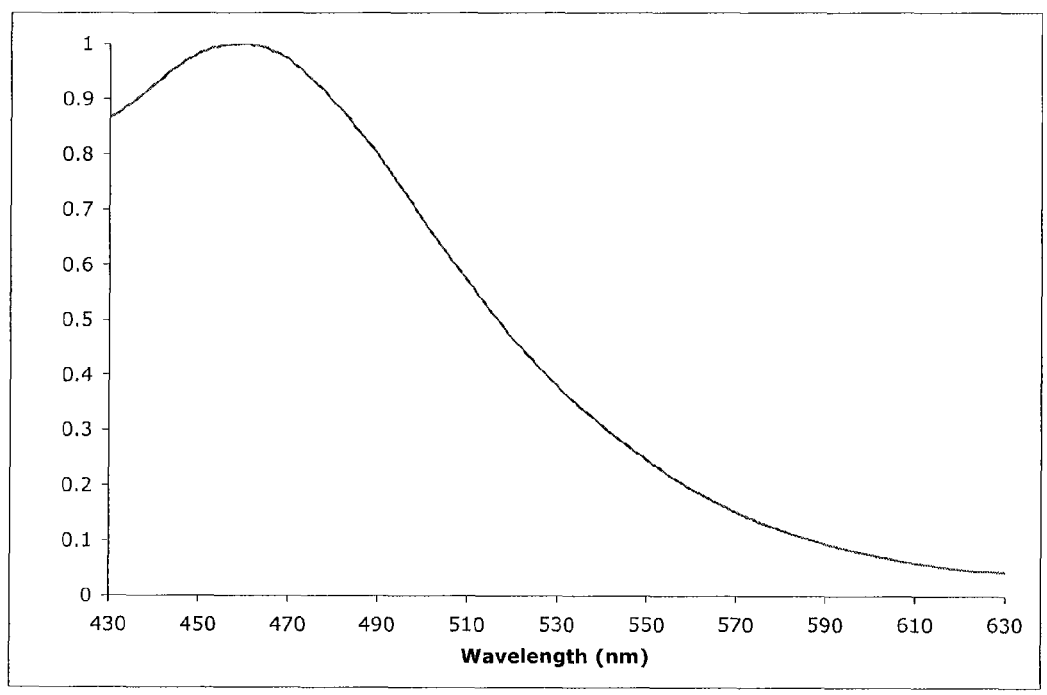
FIG. 2 shows the fluorescent emission spectrum of a product produced according to the reaction whose UV absorption properties are shown in FIG. 1.

The trans-cyclooctene adduct 13 is also fluorescent, as shown in the emission spectrum portrayed in FIG. 2 (THF, $1 \times 10^{-5}$ M). Thus, fluorescence spectroscopy can also be used as a label and a probe in tetrazine based coupling. Accordingly, exposing an adduct of a 1,2,4,5-tetrazine with a dienophile to UV radiation, and measuring either the fluorescent emission or UV absorption of the sample, can provide a method of quantitatively analyzing species present in the sample.

As a stringent test of tolerance of biological functionality, the inventors have shown that the IED-DA reaction of 4 with trans-cyclooctene can be carried out in cell media (DMEM+ 5% FBS) or in an aqueous solution containing 10% untreated rabbit reticulocyte lysate (which contains tRNA, ribosomes, amino acids, glutathione, etc). The reactions were carried out at room temperature for 1 h with 50 μM 4 and 500 μM 12, and monitored by ESI-MS. The yield in cell lysate was estimated to be 80% (vs. internal MS standard).

Kinetic Measurements

The reaction rates of tetrazine Diels-Alder reactions have been measured, and are very rapid compared with some of the canonical bioorthogonal coupling reactions. Rate measurements are shown in Table 2 below. Second order rate constants were extrapolated from rate measurements made under pseudo-first order conditions. For the Cu-catalyzed Sharpless-Huisgen reactions of benzyl azide and phenylacetylene, the reaction order was not determined. However, the Cu-catalyzed Sharpless-Huisgen reactions are slow relative to the other reactions in Table 2: half-lives of 1.0 h and 6.4 h were measured for the reactions in Entries 5A and 5B conducted at 0.16 M in azide and 1.6 M in alkyne. Details of the experiments referred to in Table 2 are given in the Examples.

TABLE 2
Entry 1
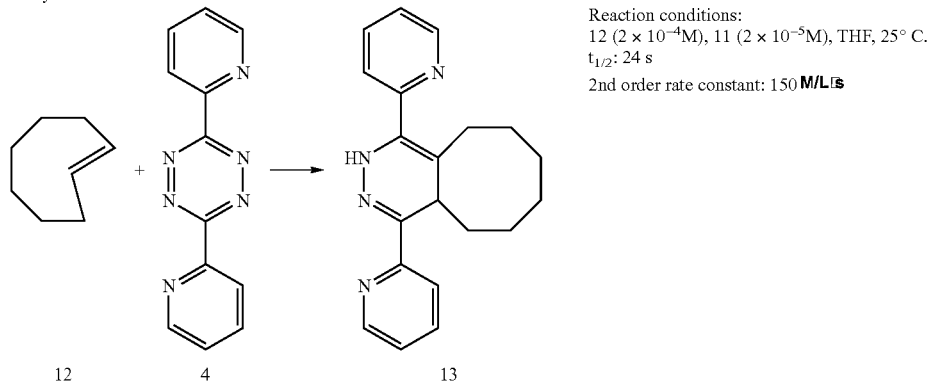
Reaction conditions:
12 (2 × 10⁻⁴M), 11 (2 × 10⁻⁵M), THF, 25° C.
$t_{1/2}$: 24 s
2nd order rate constant: 150 M/L·s
Entry 2
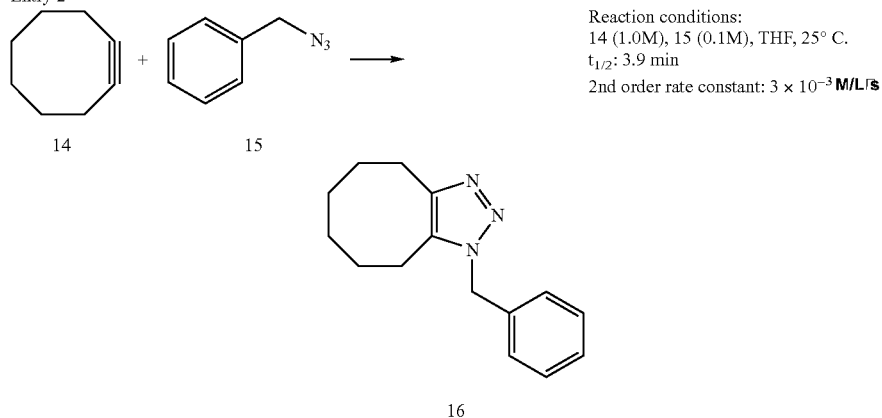
Reaction conditions:
14 (1.0M), 15 (0.1M), THF, 25° C.
$t_{1/2}$: 3.9 min
2nd order rate constant: 3 × 10⁻³ M/L·s
Entry 3
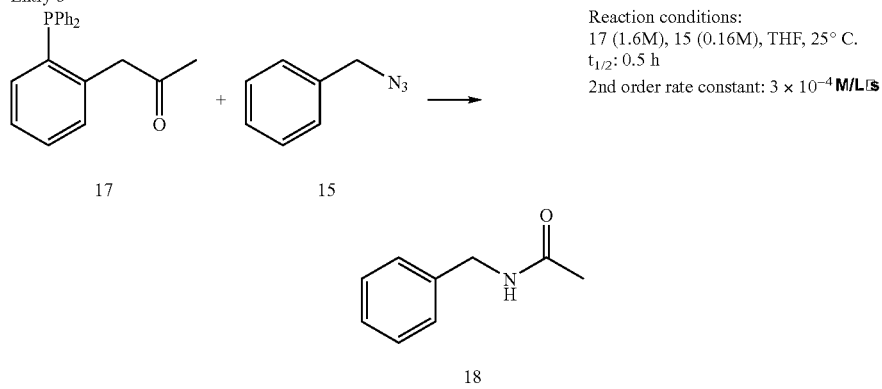
Reaction conditions:
17 (1.6M), 15 (0.16M), THF, 25° C.
$t_{1/2}$: 0.5 h
2nd order rate constant: 3 × 10⁻⁴ M/L·s
Entry 4
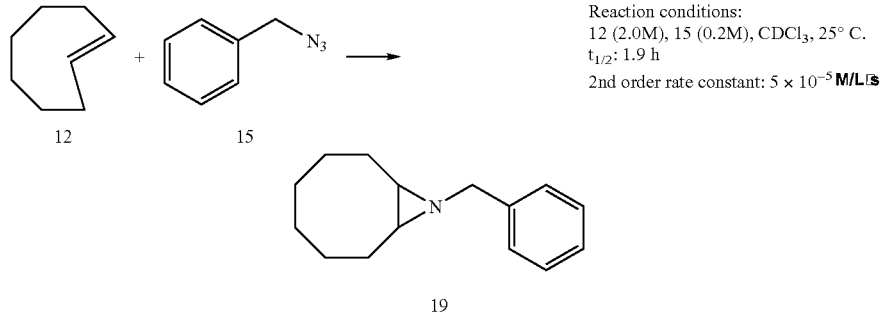
Reaction conditions:
12 (2.0M), 15 (0.2M), CDCl₃, 25° C.
$t_{1/2}$: 1.9 h
2nd order rate constant: 5 × 10⁻⁵ M/L·s

TABLE 2-continued

Entry 5

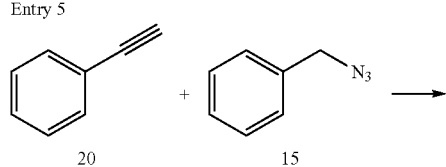

Reaction conditions A:
20 (1.6M), 15 (0.16M), 2:1 tBuOH:H$_2$O, 25° C.
1% CuSO$_4$, 10% sodium ascorbate
$t_{1/2}$: 6.4 h
Reaction conditions B:
20 (1.6M), 15 (0.16M), 2:1 tBuOH:H$_2$O, 25° C.
1% CuSO$_4$, 1% TBTA, 10% sodium ascorbate
$t_{1/2}$: 1.0 h

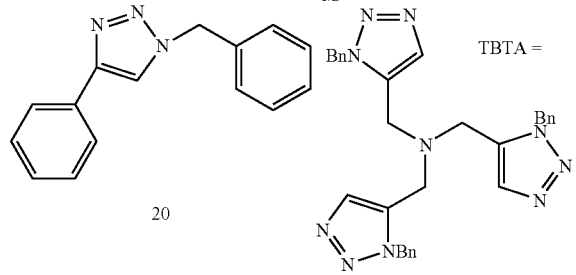

In addition to the commercially available 3,6-di-(2-pyridyl)-1,2,4,5-tetrazine (compound 4), the unsymmetrical derivative 23 of has been prepared by the inventors as shown in Scheme 5. Compound 23 is exemplary, and amides of acids other than acetic acid can be made instead according to the invention. Lower aliphatic or aromatic acids might be used, for example, but others may be used as well. The aniline functionality is suitable for attachment of functional groups, e.g., via amide linkages. Examples may include more highly fluorescent labels, biotin, and other functional groups known in the art. Nanotubes, metallic nanoparticles, and MRI contrast agents may also be attached in that manner.

Scheme 5

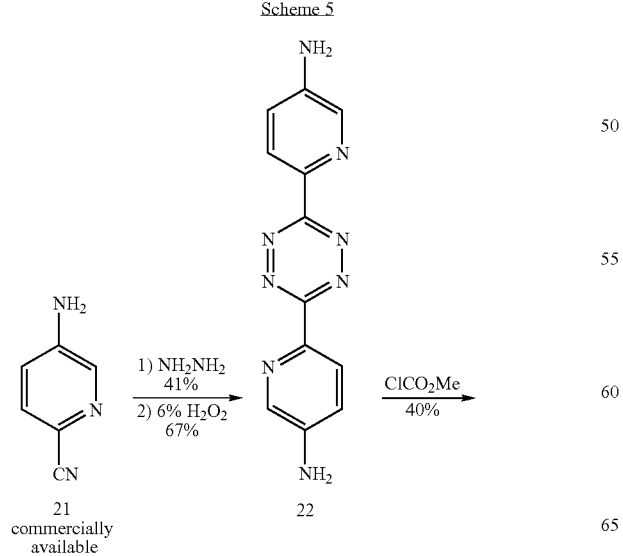

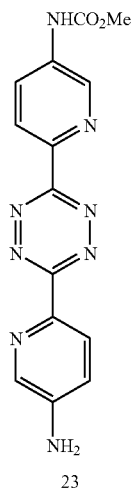

Demonstration of Tetrazine Bio-Orthogonal Coupling to Thioredoxin

5-Hydroxy-trans-cyclooctene 24 has been elaborated into carboxylic acid derivative 25, and into maleimide functionalized carbamate 26 (Scheme 6).

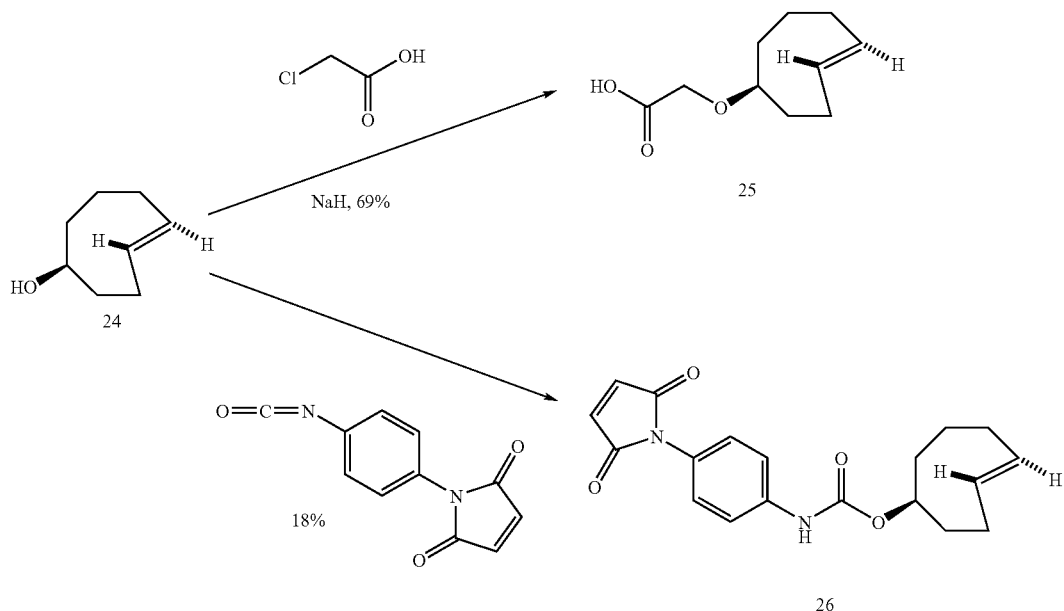

Taking advantage of its ability to react without interference from biological species such as proteins, compound 26 was used to append a UV-absorbing moiety to a protein as shown in Scheme 7. Coupling was carried out on a derivative of thioredoxin, a 11.7 kDa protein with a single disulfide linkage that can be identified by ESI-MS. Thioredoxin (8 μM) was reduced with tri(hydroxypropyl)phosphine at pH 6 to generate thiol moieties on the protein, and then reacted with 26, which contains both a trans-cyclooctene function, and a thiol reactive maleimide group.

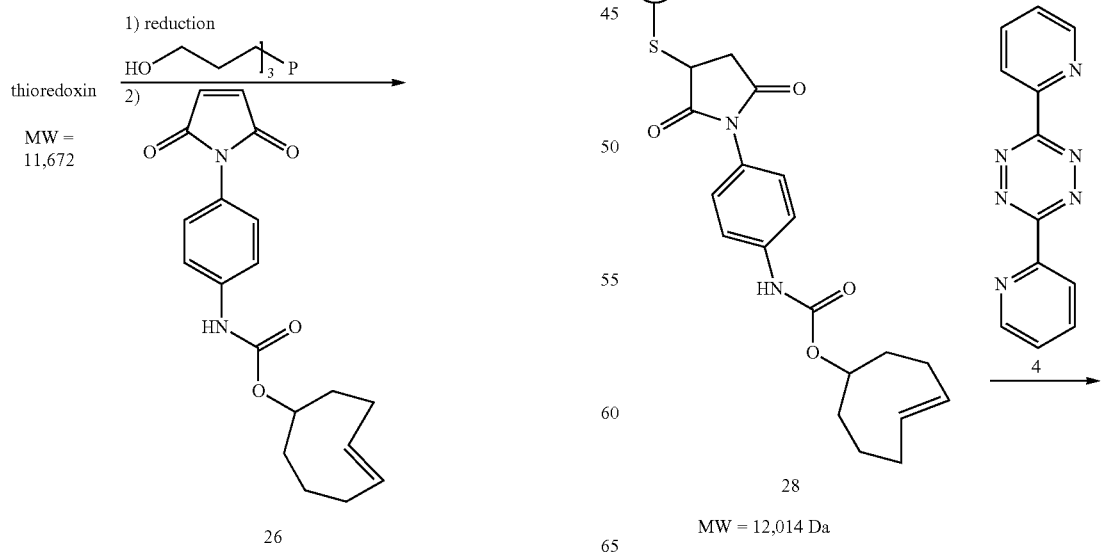

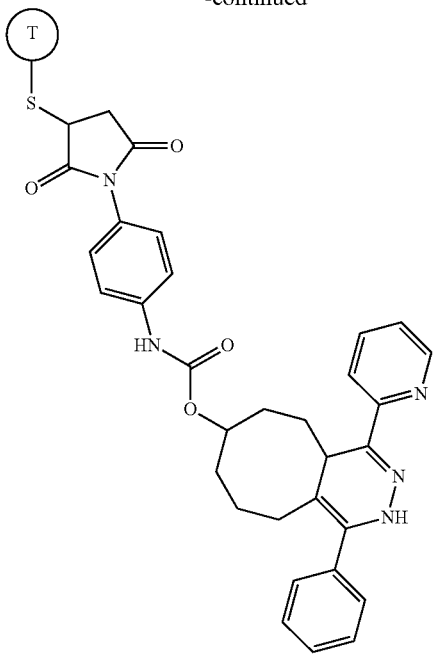

29

MW = 12,222 Da

Analysis by ESI-MS indicated that thioredoxin had reacted with a single equivalent of 26 to give an adduct 28 (in which the thioredoxin residue is indicated by the letter "T") formed by addition of the thiol moiety across the maleimide double bond of 26. Subsequent reaction of adduct 28 (diluted to 2 μM without purification) at its trans-cyclooctene moiety with 3,6-di(2-pyridyl)-1,2,4,5-tetrazine 4 (0.5 mM) gave the expected Diels-Alder cycloaddition product 29. Significantly, the reaction was completed within 5 min at room temperature; none of the peaks attributable to starting material 28 could be observed by mass spectrometry.

EXAMPLES

Photolyses were carried out using a Southern New England Ultraviolet Company: RAYONET® reactor model RPR-200, equipped with a stirring plate and 6 low pressure mercury lamps irradiating at 2537 Å. Photolyses were carried out in a 500 mL Quartz flask (Southern New England Ultraviolet Company part number RQV-323). The column used in the photolytic step were purchased from ISCO (part #69-3873-146; solid sample cartridge cap #683877061). The bottom of the column was interfaced to TEFLON® PTFE tubing flanged with nylon fittings (¼-28 thread, ⅛" OD×0.063" ID, Alltech part #20020) using a female Luer (¼-28 thread, Isco part #209016904). The pump used for recirculating solvents through the photolysis apparatus was purchased from FMI (FMI Pump Model RP-D equipped with a pumphead FMI R405).

Representative Photochemical Synthesis of Trans-Cyclooctenes: Preparation of (E)-Cyclooct-4-enol Reagent grade ethyl ether (500 mL) was added to (Z)-cyclooct-4-enol (1 g, 7.9 mmol) and methyl benzoate (1.1 g, 7.9 mmol) in a quartz flask that was equipped with a TEFLON® PTFE coated magnetic stir bar. The quartz flask was placed in a RAYONET® reactor and connected via TEFLON® PTFE tubing to a column (ISCO RediSep™, 40 g) and an FMI pump, as illustrated in FIG. 3. The column was dry packed with a 8 cm tall bed of silica. Silver nitrate impregnated silica (16.8 g, 10% w/w, 9.9 mmol of AgNO$_3$) was placed on top of the column, and the column was flushed with ether. The pump was turned on and the rate of circulation was adjusted to about 100 mL per minute. Photolysis was carried out for 8 hours. The column was washed with 200 mL of ether and dried by a stream of compressed air. The column was emptied into an Erlenmeyer flask (500 mL), and the silica gel was stirred with ammonium hydroxide (200 mL) and methylene chloride (200 mL) for 5 minutes. The silica gel was filtered, and the filtrate was transferred to a separatory funnel. The organic layer was separated, and the ammonium hydroxide layer was washed with methylene chloride (200 mL). The organic layers were combined, washed with 100 mL of water and dried with MgSO$_4$. The title product was obtained as a 2:1 mixture of diastereomers by evaporating the solvent under reduced pressure. The yield was 0.73 g (73%). A duplicate experiment gave 0.72 g (72%). The two diastereomers were separated by gravity silica column chromatography (4:1 pentane:ethyl ether) Minor diastereomer: $R_f$=0.42. Major diastereomer: $R_f$=0.30.

Competition Experiments with Benzyl Azide and Phenylacetylene

Benzyl azide (10.9 μL, 0.088 mmol) and phenylacetylene (9.6 μL, 0.088 mmol) were dissolved in THF (10 mL) and stirred at room temperature. Compound 7 (20 mg, 0.088 mmol) was added to the solution, followed compound 4 (21 mg, 0.088 mmol). The reaction mixture was stirred at room temperature for 30 minutes, during which time the purple solution turned bright yellow. TLC of the crude reaction mixture showed only adduct 11, phenylacetylene, and benzyl azide. The reaction mixture was concentrated in vacuo to yield 11 as a bright yellow solid (confirmed by $^1$H NMR).

Competition Experiment with N-Butylamine

Compounds 7 (20 mg, 0.088 mmol) and 4 (21 mg, 0.088 mmol) were dissolved in ethanol (10 mL) and stirred at room temperature. N-butylamine (8.7 μL, 0.088 mmol) was added to the solution. The reaction mixture was stirred at room temperature for 30 minutes, during which time the purple solution turned bright yellow. TLC of the crude reaction mixture showed only adduct 11 and n-butylamine. The reaction mixture was concentrated in vacuo to yield 11 as a bright yellow solid (confirmed by $^1$H NMR).

Competition Experiment with Ethanethiol

Compounds 7 (20 mg, 0.088 mmol) and 4 (21 mg, 0.088 mmol) were dissolved in ethanol and stirred at room temperature. Ethanethiol (6.5 μL, 0.088 mmol) was added to the solution. The reaction mixture was stirred at room temperature for 30 minutes, during which time the purple solution turned bright yellow. TLC of the crude reaction mixture showed only adduct 11 and ethanethiol. The reaction mixture was concentrated in vacuo to yield 11 bright yellow solid (confirmed by $^1$H NMR).

Competition Experiment with Triphenylphosphine

Compounds 7 (20 mg, 0.088 mmol) and 4 (21 mg, 0.088 mmol) were dissolved in THF (10 mL) and stirred at room temperature. Triphenylphosphine (23 mg, 0.088 mmol) was added to the solution. The reaction mixture was stirred at room temperature for 30 minutes, during which time the purple solution turned bright yellow. The reaction mixture was concentrated in vacuo. TLC of the crude reaction mixture showed only 11 and triphenylphosphine. The $^1$H NMR spectrum of the crude material showed 11. Purification by chromatography (acetone/hexanes) afforded triphenylphosphine (18.4 mg, 80% recovered) and 11 (38 mg, 99%).

UV Experiment (2.5×10$^{-6}$ M Concentration)

A 5×10$^{-6}$ M solution of compound 4 in 1:1 ethanol:H$_2$O and a 5×10$^{-6}$ M solution of compound 12 in ethanol were prepared separately. 1 mL of each solution was added to a 3-mL UV cuvette, and the absorbance was measured every five minutes at room temperature for 40 minutes. Tetrazine 4 has an absorption maximum at 292 nm, and the product 13 has an absorption maximum at 312 nm. Also, product 13 displays significant absorption at 340 nm (e=12000), whereas tetrazine 4 displays minimal absorption (e=3000) at 340 nm.

With monitoring at 292, 312 and 340 nm, the reaction was considered to be completed in 40 min.

Cell Media Experiment

A $10^{-3}$ M solution of compound 4 in 1:1 ethanol:$H_2O$ and a $10^{-2}$ M solution of compound 12 in ethanol were prepared separately. 50 μL of the $10^{-3}$ M solution of compound 4 and 50 μL of the $10^{-2}$ M solution of compound 12 were added to a glass vial containing 1 mL of cell media (DMEM, +5% FBS). The solution was stirred at room temperature for 1 hr. The solution was extracted with ether, dried over $Na_2SO_4$, filtered through celite, and concentrated in vacuo. The resulting residue was diluted with 100 μL of methanol and analyzed by ESI-MS, and compound 13 was detected Cell Lysate Experiment A $10^{-3}$ M solution of compound 4 in 1:1 ethanol:$H_2O$ and a $10^{-2}$ M solution of compound 12 in ethanol were prepared separately. 50 μL of the $10^{-3}$ M solution of compound 4 and 50 μL of the $10^{-2}$ M solution of compound 12 were added to a glass vial containing 1 mL of 10% untreated rabbit reticulocyte lysate in $H_2O$. The solution was stirred at room temperature for 1 hr. The solution was extracted with ether and $CH_2Cl_2$, dried over $Na_2SO_4$, filtered through celite, and concentrated in vacuo. The resulting residue was diluted with 100 μL of methanol and analyzed by ESI-MS and compound 13 was detected. The yield was 76% versus an internal standard.

Kinetic Experiments

All kinetic experiments were conducted under pseudo-first order conditions. The pseudo-first order rate constants were obtained by plotting the natural log of the concentration of the limiting reactant versus time in seconds. Data were plotted to 50% conversion. The second-order rate constants and half-lives were extrapolated from the rate measurements derived under pseudo-first order conditions according to the following equation, where B is the limiting reactant and A is the reactant in excess:

$$[B]=[B]_O e^{-k[A]_O t}$$

The reaction of 12 with 4 was monitored by UV-Vis, using a ten-fold excess of the dienophile. The reaction was conducted at 25° C. in a 1-mL UV cuvette. A $2\times10^{-5}$ M solution of compound 4 in THF and a $2\times10^{-4}$ M solution of compound 12 in THF were prepared separately. A 0.5 mL portion of each solution was added to the cuvette, and measurements were taken every 10 seconds until complete consumption of 4.

The reaction of 14 with 15 was monitored by GC, using a ten-fold excess of 14. Compounds 14 (100 mg, 0.741 mmol based on 80% purity), 15 (9.2 μL, 0.074 mmol), and dodecane (17 μL, 0.074 mmol) were dissolved in THF (0.74 mL) at 25° C. Aliquots of the mixture were diluted with 1 mL of $CH_2Cl_2$ and analyzed by GC every minute until 50% conversion. Dodecane was used as an internal standard to quantify the consumption of 15.

The reaction of 17 with 15 was monitored by GC, using a ten-fold excess of 17. Compounds 17 (190 mg, 0.594 mmol), 15 (7.4 μL, 0.059 mmol), and dodecane (13.3 μL, 0.059 mmol) were dissolved in THF (0.4 mL) at 25° C. Aliquots of the mixture were diluted with 1 mL of $CH_2Cl_2$ and analyzed by GC every ten minutes until 50% conversion. Dodecane was used as an internal standard to quantify the consumption of 15.

The reaction of 12 with 15 was monitored by $^1$H NMR, using a ten-fold excess of 12. Compound 15 (10 μL, 0.08 mmol) was dissolved in 0.4 mL $CDCl_3$, and data was acquired at 25° C. Compound 12 (88 mg, 0.8 mmol) was added to the solution, and data was acquired every 4 minutes for 8 hr at 25° C. The disappearance of the singlet at 4.3 ppm (methylene protons of 15) was monitored to 50% conversion.

The reaction of 20 with 15 was monitored by GC, using a ten-fold excess of 20. Compounds 20 (0.66 mL, 6.0 mmol) and 15 (0.075 mL, 0.6 mmol) were dissolved in a 2:1 mixture of tert-butanol:$H_2O$ (3 mL total). $CuSO_4$ (1.5 mg, 0.006 mmol), sodium ascorbate (60 μL of 1M solution in $H_2O$), and dodecane (0.14 mL, 0.6 mmol) were added to the reaction mixture, which was stirred at 25° C. Aliquots of the mixture were quenched with $H_2O$ and extracted with 0.2 mL of ether. The ether extract was diluted with 1 mL of $CH_2Cl_2$ and analyzed by GC every thirty minutes for the first two hours, and every hour for the remaining time until 50% conversion. Dodecane was used as an internal standard to quantify the consumption of 15.

Synthesis of 22

A resealable test tube was flushed with $N_2$ and charged with 5-amino-2-cyanopyridine (5.0 g, 42 mmol) and hydrazine hydrate (8.2 mL, 168 mmol). The tube was capped, and the mixture was heated to 85° C. for 12 hr. The reaction mixture was cooled to room temperature. The resulting orange precipitate was isolated by filtration, washed with cold $H_2O$, and dried under vacuum. The yield was 4.7 g (41%). The orange solid was dissolved in 6% $H_2O_2$ (80 mL) and heated to 60° C. The reaction mixture was stirred at this temperature overnight, during which time the orange solution turned dark red. The dark red solid formed was filtered and purified by chromatography (acetone/hexanes) to isolate recovered starting material. The residue remaining on the column was washed with methanol to afford 22 in 67% yield.

Synthesis of 23

Compound 22 (1.0 g, 3.76 mmol) was dissolved in $CH_3CN$ (20 mL) and stirred at room temperature. Methyl chloroformate (0.29 mL, 2.76 mmol) was added to the solution, which was heated to 75° C. and stirred at this temperature overnight. The reaction mixture was concentrated in vacuo. The crude residue was treated with 1% TFA to dissolve unreacted starting material, and the insoluble bright orange solid was filtered on a Buchner funnel. The orange solid was dissolved in MeOH, and 2 M KOH was added dropwise until the pH of the solution was basic. Evaporation of the solvent yielded an orange solid, which was purified by chromatography (gradient of 0-20% methanol/$CH_2Cl_2$) to afford 23 as a red solid. The yield was 196 mg (40%) based on consumed starting material.

Synthesis of 25

Sodium hydride (0.228 g, 9.51 mmol) (60% dispersion in mineral oil) was placed under nitrogen atmosphere and washed twice with 10 mL anhydrous pentane. Anhydrous tetrahydrofuran (3 mL) was added, followed by a solution of (E)-cyclooct-4-enol (0.3 g, 2.38 mmol) (minor diastereomer) in tetrahydrofuran (2 mL). The resulting solution was refluxed for one hour. Then, a solution of α-iodoacetic acid (0.442 g, 2.38 mmol) in 5 mL tetrahydrofuran was added dropwise and the reflux was continued for one hour. After cooling down to room temperature, the reaction mixture was concentrated under reduced pressure and redissolved in ethyl ether (10 mL) and 10% (w/w) aqueous KOH (10 mL). The aqueous layer was isolated, washed with ethyl ether (10 mL), and cooled down to 0° C. in the ice bath. The aqueous solution was acidified with conc. HCl and the product was extracted with 25 mL methylene chloride. The organic layer was washed brine (10 mL) and water (10 mL). The desired product was purified by flash column chromatography using a 7:3 mixture of hexanes: ethyl acetate. Yield=0.30 g (69%).

Synthesis of 26

Compound 24 (11 mg, 0.087 mmol) was dissolved in DMSO (0.64 mL), and the solution was protected from light using aluminum foil. Para-maleimidophenyl isocyanate (19 mg, 0.087 mmol) was added, and the reaction mixture was stirred at room temperature for 2 hr. Upon addition of 1 mL of $H_2O$ to the mixture, a bright orange precipitate formed. The precipitate was isolated by filtration and washed with $H_2O$. The yield was 5.4 mg (18%).

Synthesis of 28

Thioredoxin was dissolved in 2% acetic acid (1.0 mL). The initial concentration of the solution was 26 μM, which was determined by UV-Vis. Ammonium hydroxide (0.12 mL) was added to the solution until the pH reached 6.

Tri(hydroxypropyl)phosphine was added to a concentration of 2 mM, and the solution was stirred at room temperature for 12 hr. Compound 26 was added to a concentration of 4 mM, and the solution was analyzed by ESI-MS immediately following the addition.

Synthesis of 29

An 8 uM solution of adduct 28 (0.2 mL) was diluted to 2 uM with $H_2O$ (0.6 mL). Compound 4 in DMSO was added to the solution to a concentration 0.5 mM, and the solution was analyzed by ESI-MS immediately following the addition.

Cycloprop-2-enecarboxylic acid (6)

A flame-dried 1 L round bottomed flask containing $Rh_2(OAc)_4$ (120 mg, 0.271 mmol) in 800 mL $CH_2Cl_2$ was cooled by a bath of ice water. The flask was swept with $N_2$. The $N_2$ was then turned off, and the solution was sparged with acetylene gas (acetone was removed from the acetylene by first passing through two cold traps (−60~−65° C.) for 30 mins. Ethyl diazoacetate (≦15% $CH_2Cl_2$, 10.0 mL, 73 mmol) was added over the course of 5 hours via syringe pump at 0° C. The color of the mixture was dark green while ethyl diazoacetate was added. In some runs, the reaction color turned yellow or light red during the last hour of the addition, but this did not affect the yield significantly. After the addition of ethyl diazoacetate was complete, the acetylene was turned off, and the mixture was sparged with $N_2$ for about 20 minutes followed by filtration through a short silica gel plug to remove the $Rh_2(OAc)_4$. Without removal of solvent, the light yellow filtrate was transferred to a 2 L round bottomed flask. The flask was cooled by an ice bath, and methanol (800 mL) was added. A freshly made aqueous KOH solution (20 grams in 200 mL $H_2O$) was added dropwise, the homogeneous yellow mixture was allowed to stir overnight under $N_2$. (Note: Any alkali metal hydroxide can be used in place of KOH.) TLC analysis was conducted to ensure that the hydrolysis was complete. Solvents ($CH_2Cl_2$, methanol) were then removed on the rotary evaporator. Methyl-tert-butyl ether (300 mL) was then added, and the mixture was cooled by an ice bath. Aqueous HCl solution (3M) was added dropwise until the aqueous phase was rendered acidic, and solid NaCl was added until the aqueous layer was saturated. The aqueous layer was extracted twice with 300 mL portions of methyl-tert-butyl ether. The combined organics were dried over $Na_2SO_4$, filtered, and concentrated. The residue was subjected to flash chromatography on a short silica gel column (3" high×3" diameter) (diethyl ether). The product was collected and concentrated. $^1H$ NMR analysis of the colorless solution (9.1 g) indicated that it contained approx. 2.8 g (33 mmol, 44%) of 6, 3.0 g of diethyl ether and 3.3 g of MTBE. Compound 6 can also be isolated in a pure form as a hydroscopic white solid by concentrating the above solution to dryness. m.p.=40-41° C.

Synthesis of (4S)-4-phenyl-3-(cycloprop-2-en-1-oyl) oxazolidinone (7)

A flame-dried 1 L round bottomed flask containing an MTBE solution of 6 (2.8 g, 33 mmol), and 800 mL of THF was chilled by a cold bath at −30° C. (dry ice/30% ethanol in ethylene glycol). The mixture was allowed to stir under nitrogen atmosphere. Distilled triethylamine (12.2 g, 17.0 mL, 120 mmol), and pivaloyl chloride (6.0 g, 6.2 mL, 50 mmol) were added sequentially, and stirring at −30° C. was continued for one hour. LiCl (7.0 g, 170 mmol) was added. After five minutes, (S)-4-phenyloxazolidinone (9.8 g, 60 mmol), and 4-dimethylamino pyridine (408 mg, 3.35 mmol) were added. The whole reaction mixture was allowed to stir overnight at room temperature. The solvents were removed under reduced pressure, and the residue was partitioned between 300 mL of $CH_2Cl_2$ and 300 mL water. The aqueous layer was extracted twice with 300 mL portions of $CH_2Cl_2$, and the combined organics were dried ($Na_2SO_4$), filtered, and concentrated. The residue was chromatographed on silica gel. The initial eluent was 1:1:9 $CH_2Cl_2$:ethyl acetate:hexane, followed by elution with 1:3:7 $CH_2Cl_2$:ethyl acetate:hexane. The yield of 7 was 7.20 g (31.5 mmol, 95%). Compound 7 is a white solid. mp=118-119° C., $[\alpha]_D$+140.0 (c 1.00, THF).

Synthesis of 3-[cycloprop-2-en-1-oyl]-oxazolidinone (8)

A flame-dried 100 mL round bottomed flask containing 6 (84 mg, 1.0 mmol), 20 mL of THF was chilled by a cold bath at −30° C. (dry ice/30% ethanol in ethylene glycol). The mixture was allowed to stir under nitrogen atmosphere. Distilled triethylamine (0.36 g, 0.50 mL, 3.5 mmol), 1-adamantyl chloride (238 mg, 1.2 mmol) were added sequentially, and stirring at −30° C. was continued for one hour. LiCl (0.21 g, 5.0 mmol) was added. After five minutes, oxazolidinone (131 mg, 1.50 mmol), and 4-dimethylamino pyridine (13 mg, 0.10 mmol) were added. The whole reaction mixture was allowed to stir overnight at room temperature. The solvents were removed under reduced pressure, and the residue was partitioned between 20 mL of $CH_2Cl_2$ and 20 mL water. The aqueous layer was extracted twice with 20 mL portions of $CH_2Cl_2$, and the combined organics were dried ($Na_2SO_4$), filtered, and concentrated. The residue was chromatographed on silica gel. The eluent was 1:3:6 $CH_2Cl_2$:ethyl acetate: hexane. The yield of 8 was 115 mg (0.752 mmol, 75%). Compound 8 is a semi-solid.

Synthesis of 3-(Cycloprop-2-enecarbonyl)-3H-benzoxazol-2-one (27)

A flame-dried 100 mL round bottomed flask containing 6 (84 mg, 1.0 mmol) and 20 mL of THF was chilled by a cold bath at −30° C. (dry ice/30% ethanol in ethylene glycol). The mixture was allowed to stir under nitrogen atmosphere. Distilled triethylamine (0.36 g, 0.50 mL, 3.5 mmol) and 1-adamantyl chloride (238 mg, 1.2 mmol) were added sequentially, and stirring at −30° C. was continued for one hour. LiCl (0.21 g, 5.0 mmol) was added. After five minutes, 2-benzoxazolinone (203 mg, 1.50 mmol), and 4-dimethylamino pyridine (13 mg, 0.10 mmol) were added. The whole reaction mixture was allowed to stir overnight at room temperature. The solvents were removed under reduced pressure, and the residue was partitioned between 20 mL of $CH_2Cl_2$, and 20 mL water. The aqueous layer was extracted twice with 20 mL portions of $CH_2Cl_2$, and the combined organics were dried ($Na_2SO_4$), filtered, and concentrated. The residue was chromatographed on silica gel. The eluent was 1:3:6 CH$_2$Cl$_2$:ethyl acetate:hexane. The yield of 27 was 161 mg (0.80 mmol, 80%). Compound 27 is a white solid.

Synthesis of 3-(5-Aminopyridin-2-yl)-6-(pyridin-2-yl)-1,2,4,5-tetrazine (30)

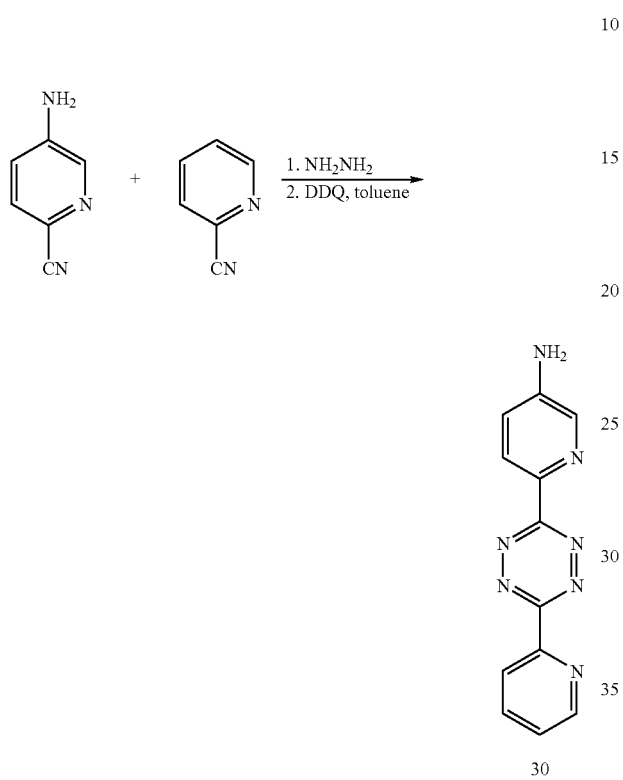

30

A dry round-bottom flask was charged with 2-cyanopyridine (0.500 g, 4.8 mmol), 5-amino-2-cyanopyridine (0.572 g, 4.8 mmol), and 64% aqueous hydrazine hydrate (0.932 mL, 19.2 mmol). The flask was fitted with a reflux condenser, and the mixture was heated to 90° C. for 12 hr. The reaction mixture was cooled to room temperature. The resulting orange precipitate was isolated by filtration, washed with cold H$_2$O, and dried under vacuum. The crude orange solid was concentrated in vacuo onto deactivated silica gel and chromatographed using a gradient (0-60%) of acetone in hexanes to give 377 mg (1.5 mmol, 31%) of 6-(6-pyridin-2-yl-1,4-dihydro-[1,2,4,5]tetrazin-3-yl)-pyridin-3-ylamine as an orange solid, mp 158-160° C.

To a solution of 3-(5-aminopyridin-2-yl)-6-(pyridin-2-yl)-1,4-dihydro-1,2,4,5-tetrazine (0.950 g, 3.8 mmol) in anhydrous toluene (25 mL) under N$_2$ was added 2,3-dichloro-5,6-dicyanobenzoquinone (1.7 g, 7.5 mmol). The reaction mixture was allowed to reflux and stir for 12 hr. The reaction mixture was concentrated under reduced pressure, and the crude residue was concentrated in vacuo onto deactivated silica gel and chromatographed using a gradient (0-100%) of acetone in hexanes to give 771 mg (3.1 mmol, 81%) of the title compound as a red solid, mp 207-209° C.

Synthesis of N-benzoyl-3-(5-aminopyridin-2-yl)-6-(pyridin-2-yl)-1,2,4,5-tetrazine (31)

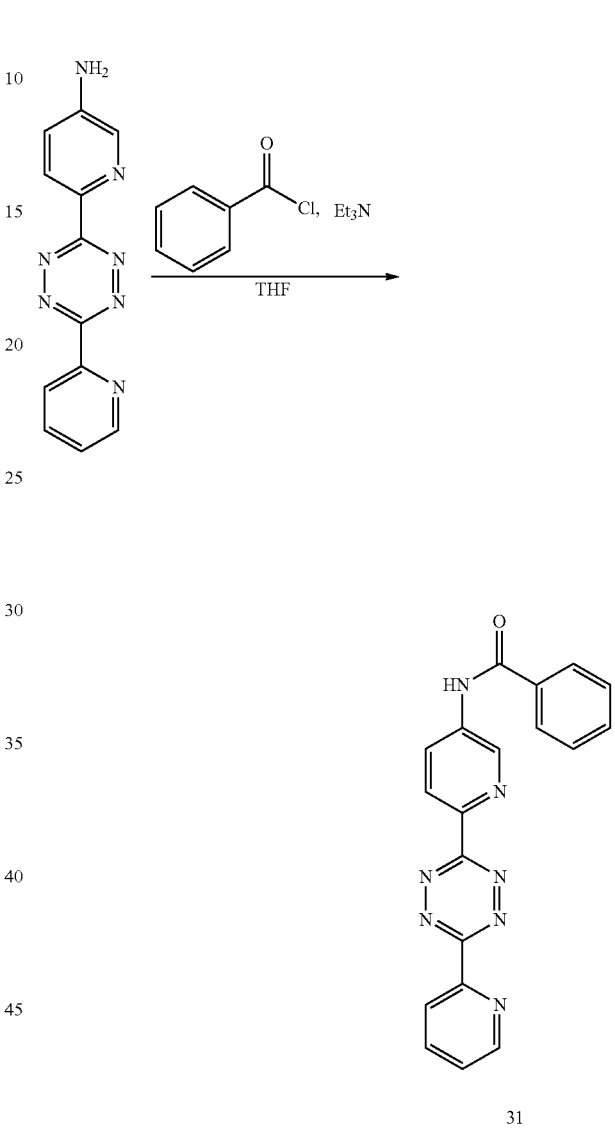

31

A resealable test tube was flushed with N$_2$ and charged with 8 (0.038 g, 0.15 mmol) and anhydrous THF (1.5 mL). Et$_3$N (0.031 mL, 0.23 mmol) and benzoyl chloride (0.088 mL, 0.76 mmol) were added via syringe, the test tube was capped, and the mixture was heated to 70° C. The reaction mixture was stirred for 1 h and concentrated under reduced pressure. The crude residue was triturated twice with hexanes and twice with toluene to remove the excess benzoyl chloride, and then concentrated in vacuo onto silica gel and chromatographed using a gradient (0-100%) of acetone in hexanes as the eluent to give 41 mg (0.12 mmol, 76%) of the title compound as a pink solid, mp 223-225° C.

Synthesis of N-acetyl-3-(5-aminopyridin-2-yl)-6-(pyridin-2-yl)-1,2,4,5-tetrazine (32)

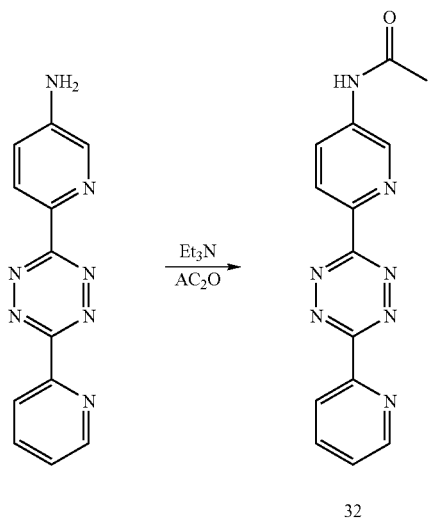

A dry round-bottom flask was charged with 3-(5-aminopyridin-2-yl)-6-(pyridin-2-yl)-1,2,4,5-tetrazine (0.020 g, 0.08 mmol) and cooled to 0° C. Et$_3$N (0.012 mL, 0.12 mmol) was added followed by Ac$_2$O (0.6 mL), which was added dropwise via syringe. The reaction mixture was allowed to stir at room temperature for 3 h and then concentrated under reduced pressure. The crude residue was chromatographed on silica gel using a gradient (0-100%) of acetone in hexanes as the eluent to give 13 mg (0.04 mmol, 56%) of the title compound as a reddish pink solid.

Synthesis of N-maleyl-3-(5-aminopyridin-2-yl)-6-(pyridin-2-yl)-1,2,4,5-tetrazine (33)

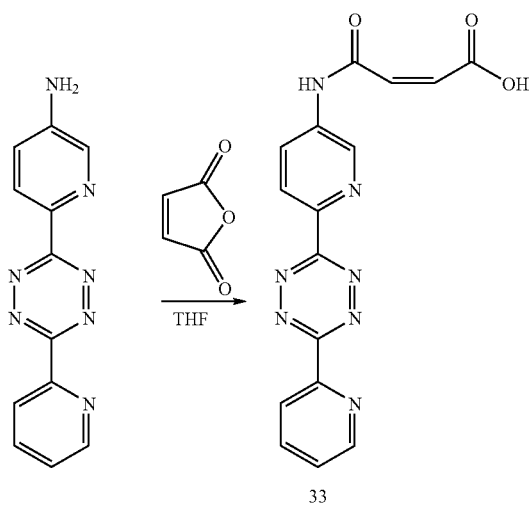

A resealable test tube was flushed with N$_2$ and charged with 3-(5-aminopyridin-2-yl)-6-(pyridin-2-yl)-1,2,4,5-tetrazine (0.2 g, 0.80 mmol), maleic anhydride (0.39 g, 4.0 mmol) and anhydrous THF (8 mL). The test tube was capped, and the mixture was heated to 70° C. and allowed to stir at this temperature for 16 h. The reaction was concentrated under reduced pressure, and the crude residue was triturated twice with methylene chloride and twice with ethyl acetate to remove the excess maleic anhydride. The solid was filtered and dried under vacuum to give 205 mg (0.59 mmol, 74%) of the title compound as a red solid.

Synthesis of N-succinyl-3-(5-aminopyridin-2-yl)-6-(pyridin-2-yl)-1,2,4,5-tetrazine (34)

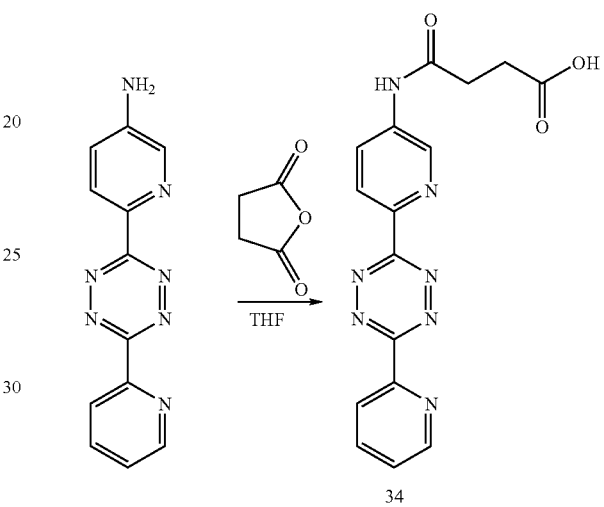

A resealable test tube was flushed with N$_2$ and charged with 3-(5-Aminopyridin-2-yl)-6-(pyridin-2-yl)-1,2,4,5-tetrazine (0.030 g, 0.12 mmol), succinic anhydride (0.060 g, 0.60 mmol) and anhydrous THF (1.2 mL). The test tube was capped, and the mixture was heated to 70° C. and allowed to stir at this temperature for 16 h. The reaction was concentrated under reduced pressure, and the crude residue was triturated twice with methylene chloride and twice with ethyl acetate to remove the excess succinic anhydride. The solid was filtered and dried under vacuum to give 24 mg (0.068 mmol, 57%) of the title compound as a red solid.

Synthesis of 1,4-diphenyl-5,6,7,8,9,10-hexahydrocycloocta[d]pyridazine (35)

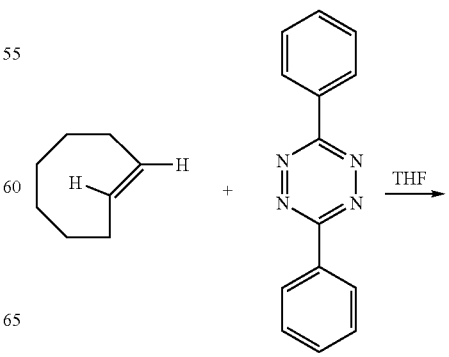

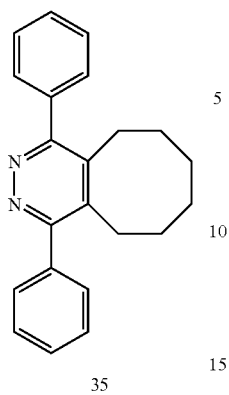

35

A dry round-bottomed flask was charged with 3,6-diphenyl-1,2,4,5-tetrazine (0.030 g, 0.13 mmol) and the flask was evacuated and filled with nitrogen. Anhydrous THF (1.3 mL) and trans-cyclooctene (0.014 g, 0.21 mmol) were added to the reaction mixture. After approximately 20 minutes the purple solution turned yellow, indicating that the reaction had gone to completion. The reaction mixture was concentrated under reduced pressure. The crude yellow residue was chromatographed on silica gel using a gradient (0-50%) of EtOAc in hexanes as the eluent to give 38 mg (95%) of the title compound as a pale yellow solid, mp 163-165° C. The adduction product had aromatized upon workup and chromatography to provide the titled compound.

Although the invention is illustrated and described herein with reference to specific embodiments, the invention is not intended to be limited to the details shown. Rather, various modifications may be made in the details within the scope and range of equivalents of the claims without departing from the invention.

What is claimed:

1. A method of performing a coupling reaction, comprising contacting a 1,2,4,5-tetrazine with a dienophile in an organic or aqueous medium comprising at least one species selected from the group consisting of primary amines, thiols, Staudinger reactants, Staudinger adducts, Sharpless-Huisgen reactants, and Sharpless-Huisgen adducts; said contacting performed under conditions sufficient to convert at least 50% of the 1,2,4,5-tetrazine or the dienophile to a Diels-Alder adduct of the 1,2,4,5-tetrazine with the dienophile; wherein the dienophile is selected from the group consisting of trans-cyclooctene, substituted trans-cyclooctenes and compounds according to formulas (7), (8) and (27)

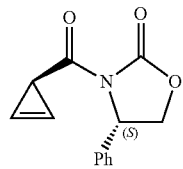

7

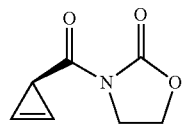

8

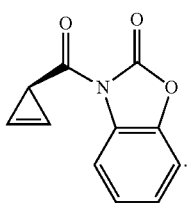

27

2. The method of claim 1, wherein the conversion is at least 90%.

3. The method of claim 1, wherein the conditions comprise a temperature of at most 50° C. and a reaction time of at most 1 hour.

4. The method of claim 1, wherein a concentration of the 1,2,4,5-tetrazine or the dienophile in the medium is at most 0.01M.

5. The method of claim 1, wherein the medium is an aqueous medium.

6. The method of claim 1, wherein the medium is a biological medium.

7. The method of claim 1, wherein the 1,2,4,5-tetrazine is selected from the group consisting of compounds according to formulas (4), (22), (23), (30), (31), (32), (33) and (34)

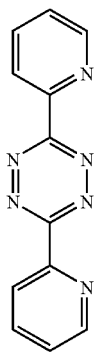

4

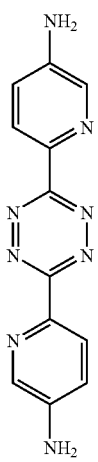

22

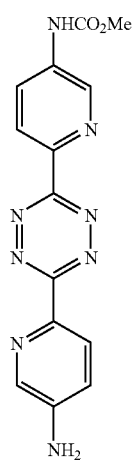
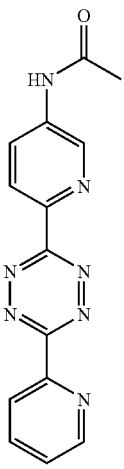
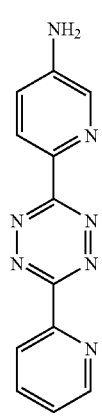
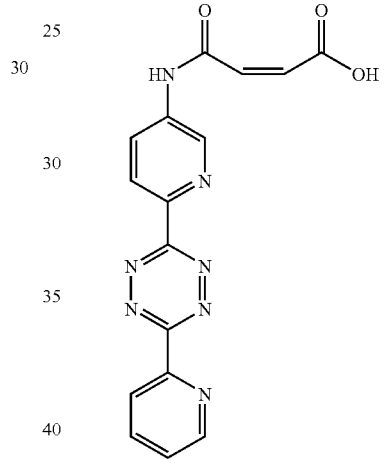
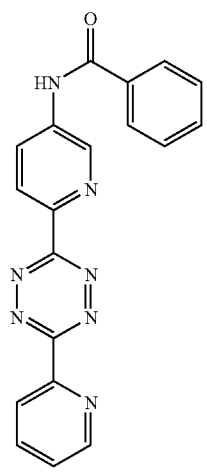
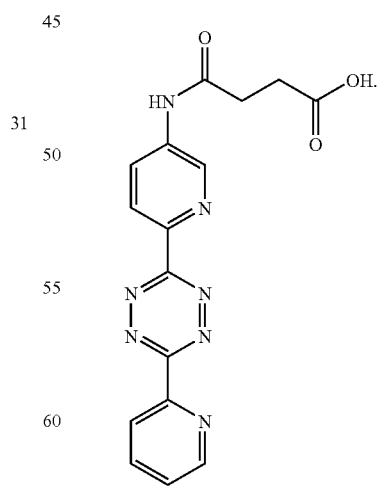
8. The method of claim 1, wherein the dienophile is selected from the group consisting of compounds according to formulas (7), (8) and (27)

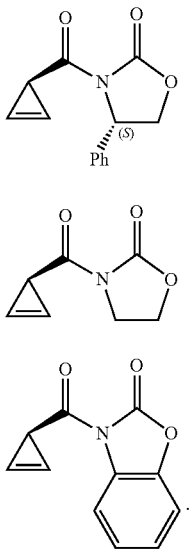

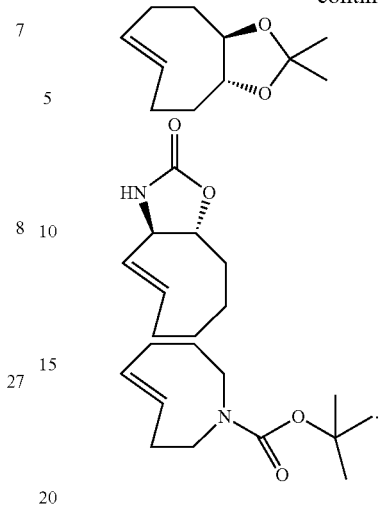

9. The method of claim 1, wherein the dienophile is trans-cyclooctene.

10. The method of claim 1, wherein the dienophile is a substituted trans-cyclooctene.

11. The method of claim 1, wherein the dienophile is a substituted trans-cyclooctene selected from the group consisting of the following compounds

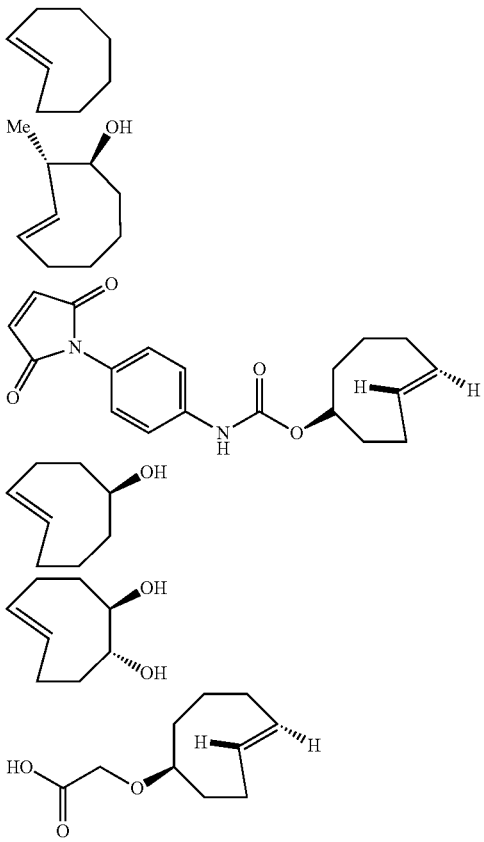

12. The method of claim 1, wherein the medium comprises a Staudinger reactant or a Sharpless-Huisgen reactant, the method further comprising subsequently contacting the Staudinger reactant or a Sharpless-Huisgen reactant with a complementary reactant under conditions sufficient to convert at least 50% of the Staudinger reactant, the Sharpless-Huisgen reactant, or the complementary reactant to a Staudinger adduct or a Sharpless-Huisgen adduct.

13. A method of performing a coupling reaction, comprising contacting a 1,2,4,5-tetrazine with a dienophile in an organic or aqueous medium; said contacting performed under conditions sufficient to convert at least 50% of the 1,2,4,5-tetrazine or the dienophile to a Diels-Alder adduct of the 1,2,4,5-tetrazine with the dienophile, wherein the dienophile is covalently bonded to a protein and wherein the dienophile is selected from the group consisting of trans-cyclooctene, substituted trans-cyclooctenes and compounds according to formulas (7), (8) and (27)

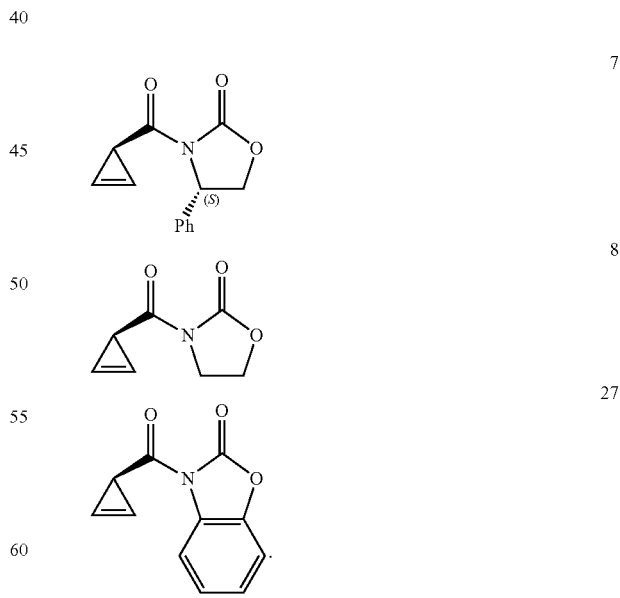

14. A method of performing a coupling reaction, comprising contacting a 1,2,4,5-tetrazine selected from the group consisting of compounds according to formulas (4), (22), (23), (30), (31), (32), (33) and (34)

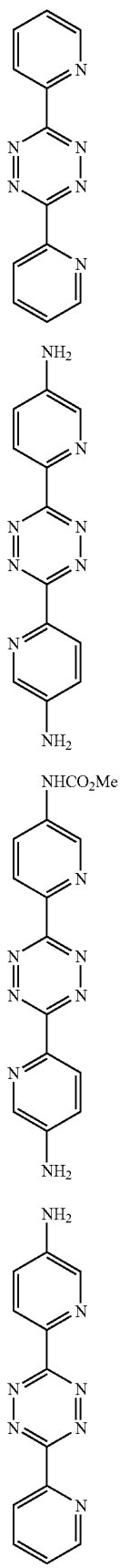
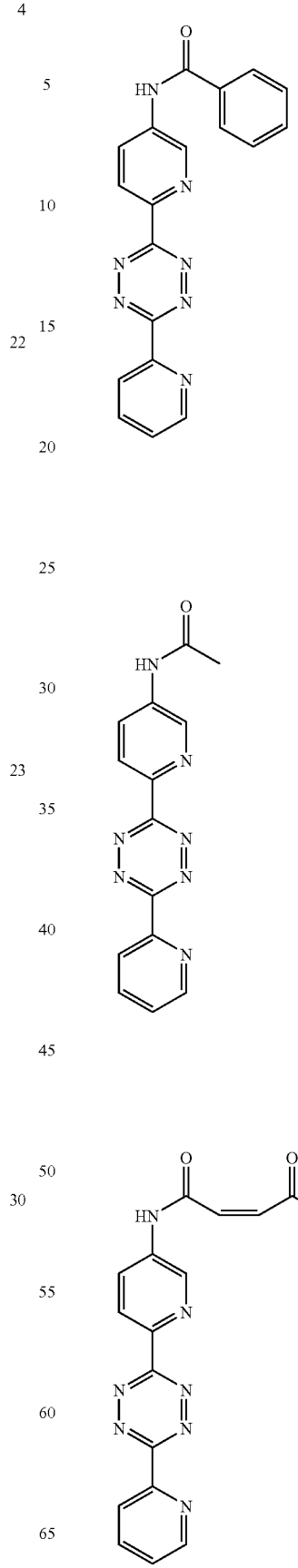

-continued

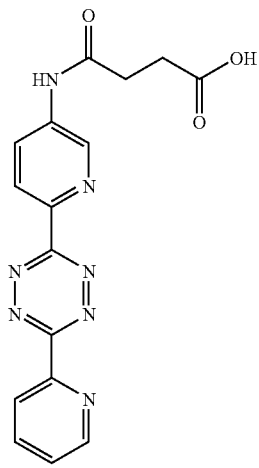
34 with a substituted cyclopropene selected from the group consisting of compounds according to formulas (7), (8) and (27)

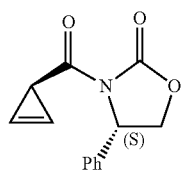
7

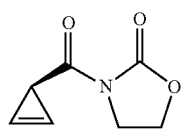
8

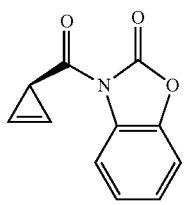
27 in an organic or aqueous medium under conditions sufficient to convert at least 50% of the 1,2,4,5-tetrazine or the substituted cyclopropene to a Diels-Alder adduct of the 1,2,4,5-tetrazine with the substituted cyclopropene.

15. The method of claim 14, wherein the medium is an aqueous medium.

16. The method of claim 14, wherein the medium is a biological medium.

17. A method of performing a coupling reaction, comprising contacting a 1,2,4,5-tetrazine selected from the group consisting of compounds according to formulas (4), (22), (23), (30), (31), (32), (33) and (34)

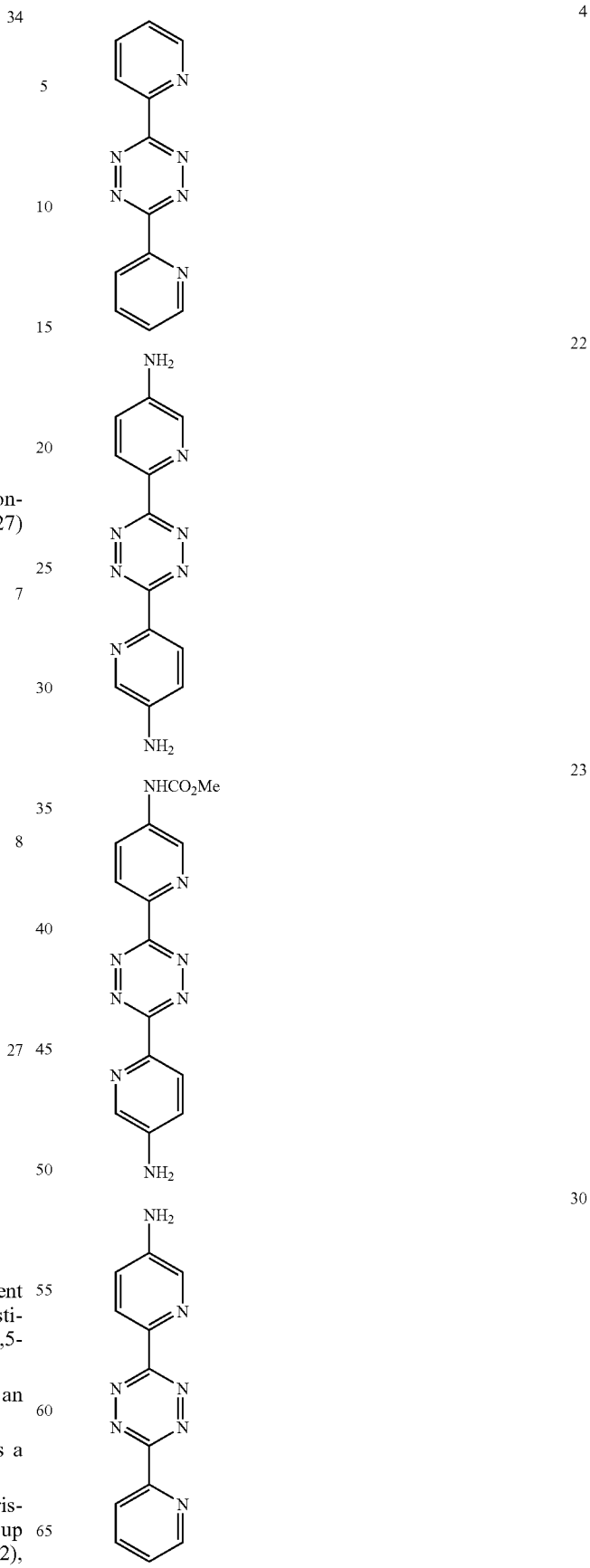

31

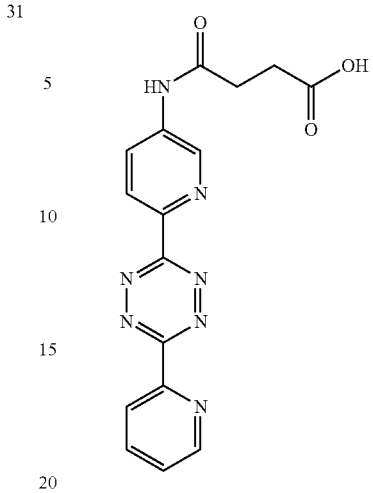

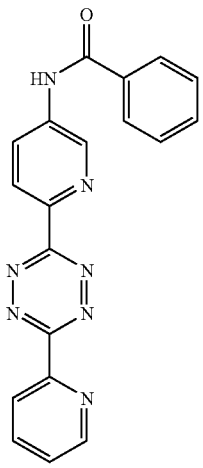

with trans-cyclooctene or a substituted trans-cyclooctene in an organic or aqueous medium under conditions sufficient to convert at least 50% of the 1,2,4,5-tetrazine, the trans-cyclooctene, or the substituted trans-cyclooctene to a Diels-Alder adduct of the 1,2,4,5-tetrazine with the trans-cyclooctene or the substituted trans-cyclooctene.

18. The method of claim 17, wherein the contacting is performed with trans-cyclooctene.

19. The method of claim 17, wherein the contacting is performed with a substituted trans-cyclooctene selected from the group consisting of the following compounds

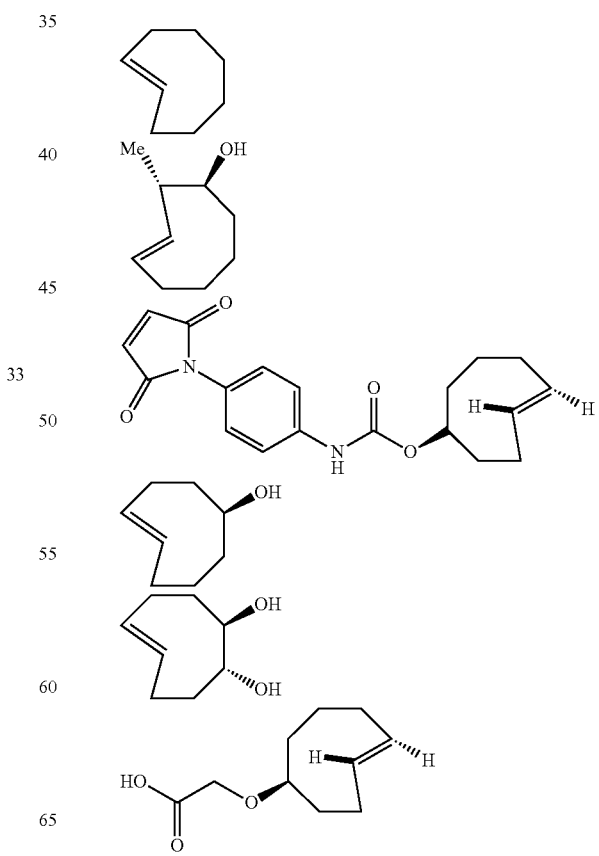

32

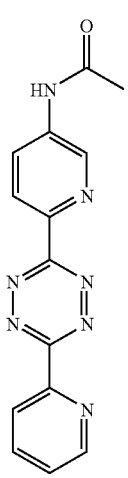

33

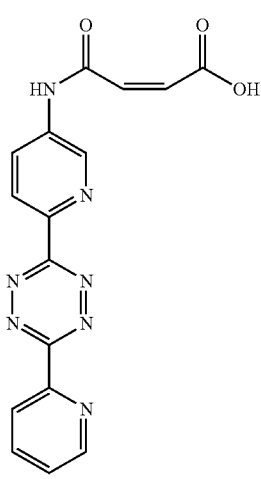

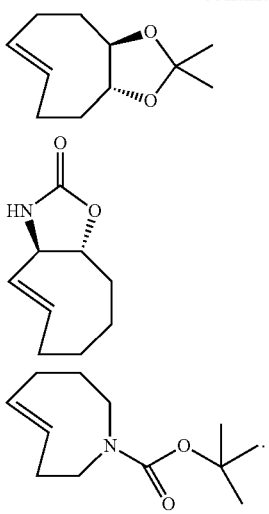
20. A 1,2,4,5-tetrazine selected from the group consisting of compounds according to formulas (22), (23), (30), (31), (32), (33) and (34)
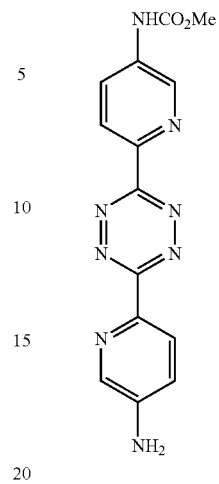
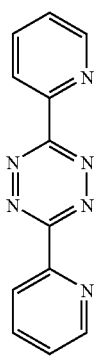
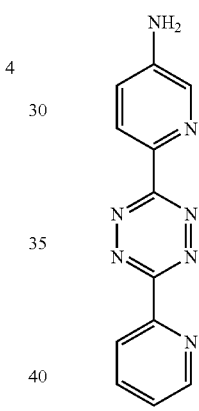
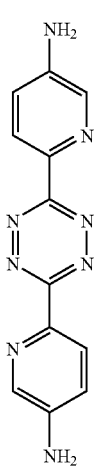
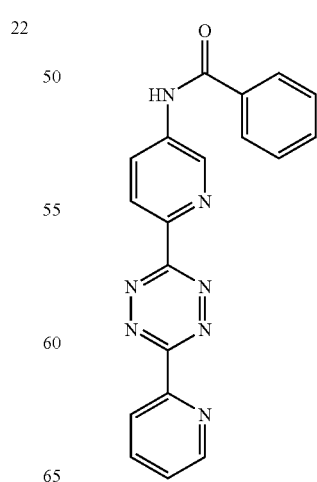

32
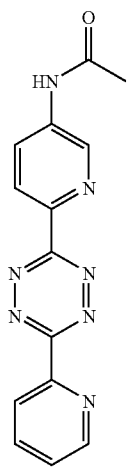
22
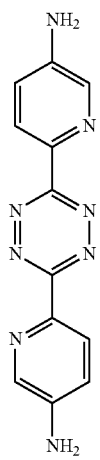
33
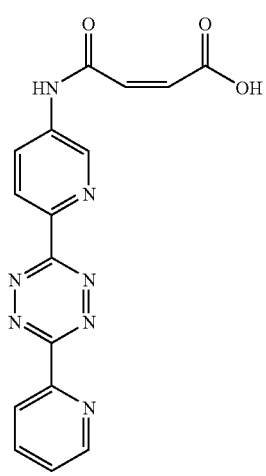
23
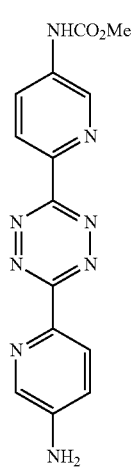
34
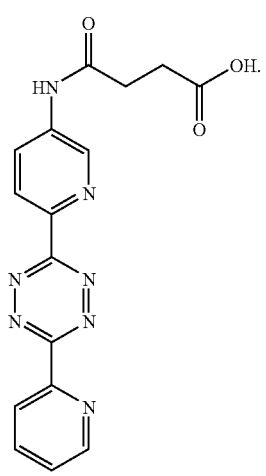
30
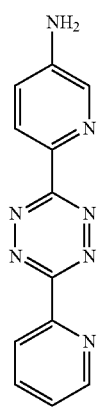

31
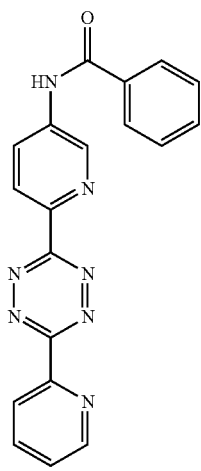
32
33
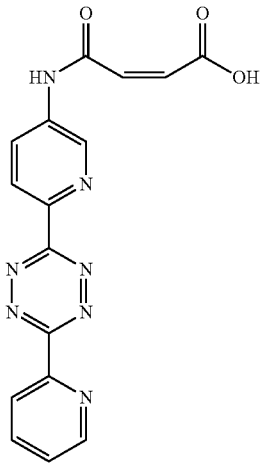
34
21. A method of quantitative analysis comprising the steps of exposing an adduct of a 1,2,4,5-tetrazine with a dienophile to UV radiation, and measuring either the fluorescent emission or UV absorption of the sample.
22. The method of claim 13, wherein the dienophile comprises a trans-cyclooctene moiety.
* * * * *

UNITED STATES PATENT AND TRADEMARK OFFICE
CERTIFICATE OF CORRECTION

PATENT NO. : 8,236,949 B2
APPLICATION NO. : 12/174913
DATED : August 7, 2012
INVENTOR(S) : Joseph Michael Fox et al.

It is certified that error appears in the above-identified patent and that said Letters Patent is hereby corrected as shown below:

In the Specification

Delete structures 4, 22, 23, 30 – 34 in columns 49-51 as shown on attached pages.

Signed and Sealed this
Third Day of June, 2014

Michelle K. Lee
*Deputy Director of the United States Patent and Trademark Office*

CERTIFICATE OF CORRECTION (continued)
U.S. Pat. No. 8,236,949 B2

-continued

23

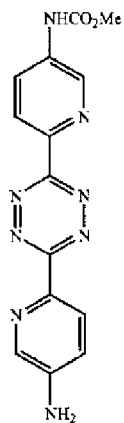

4

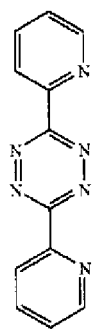

30

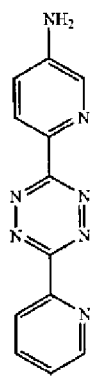

22

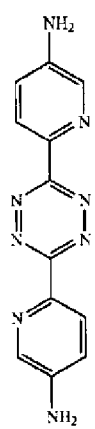

31

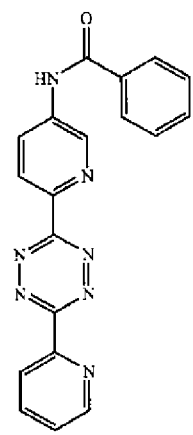

"

-continued
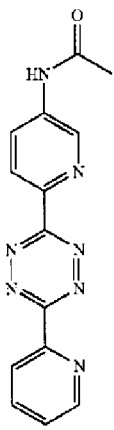
32
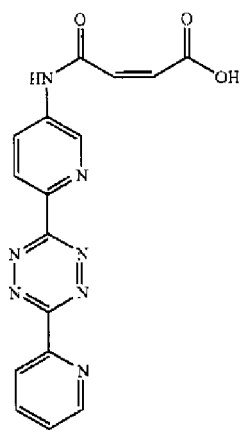
33
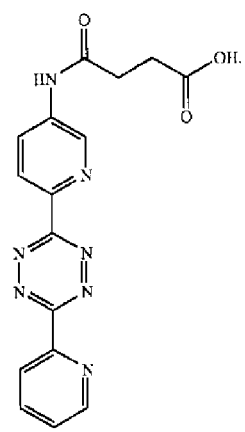
34